US006458584B1

(12) United States Patent
Mirzabekov et al.

(10) Patent No.: US 6,458,584 B1
(45) Date of Patent: Oct. 1, 2002

(54) CUSTOMIZED OLIGONUCLEOTIDE MICROCHIPS THAT CONVERT MULTIPLE GENETIC INFORMATION TO SIMPLE PATTERNS, ARE PORTABLE AND REUSABLE

(75) Inventors: Andrei Mirzabekov, Darien, IL (US); Dmitry Y. Guschin, Rockville, MD (US); Valentine Chik, Woodridge, IL (US); Aleksei Drobyshev, Elektrosol (RU); Alexander Fotin, Cambridge, MA (US); Gennadiy Yershov; Yuri Lysov, both of Hinsdale, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/261,115

(22) Filed: Mar. 3, 1999

(Under 37 CFR 1.47)

Related U.S. Application Data

(63) Continuation-in-part of application No. 08/780,026, filed on Dec. 23, 1996, now abandoned.

(51) Int. Cl.[7] .............................. C12M 1/34; C12Q 1/68; C12P 19/34; C07H 21/02; C07H 19/00
(52) U.S. Cl. ..................... 435/287.2; 435/6; 435/7.1; 435/91.1; 435/91.2; 435/287.2; 536/22.1; 536/23.1; 536/24.3; 536/24.31; 536/24.32; 536/24.33
(58) Field of Search ...................... 435/6, 7.1, 91.1, 435/91.2, 287.2; 536/22.1, 23.1, 24.3–24.33

(56) References Cited

U.S. PATENT DOCUMENTS

| 5,462,855 A | 10/1995 | Springer et al. | |
| 5,466,577 A | 11/1995 | Weisburg | 435/6 |
| 5,495,008 A | 2/1996 | Lane et al. | 536/24.3 |
| 5,552,270 A | 9/1996 | Khrapko et al. | |
| 5,593,839 A | 1/1997 | Hubbell et al. | 435/6 |
| 5,624,711 A | 4/1997 | Sundberg et al. | 427/261 |
| 5,770,721 A | 6/1998 | Ershov et al. | 236/25.3 |

FOREIGN PATENT DOCUMENTS

| EP | 0 535 242 A1 | 3/1992 |
| WO | WO 89/11548 | 11/1989 |
| WO | WO 90/15157 | 12/1990 |
| WO | WO 95/00530 | 1/1995 |
| WO | WO 96/08582 | 3/1996 |
| WO | WO 96/36733 | 11/1996 |
| WO | WO 97/29212 | 8/1997 |
| WO | WO 98/12354 | 3/1998 |
| WO | WO 98/28444 | 7/1998 |

OTHER PUBLICATIONS

Teski et al J. of Bact. vol. 176 No. 21 pp. 6623–6630 1994.*

Borman, S. (1996) "DNA Chips Come of Age After Period of Gestation, Technology for Genetic Analysis is Blossiming." *Chemical and Engineering News*, 74(50): 42–43.

(List continued on next page.)

*Primary Examiner*—Jeffrey Siew
(74) *Attorney, Agent, or Firm*—Barnes & Thornburg; Alice O. Martin

(57) ABSTRACT

This invention relates to using customized oligonucleotide microchips as biosensors for the detection and identification of nucleic acids specific for different genes, organisms and/or individuals in the environment, in food and in biological samples. The microchips are designed to convert multiple bits of genetic information into simpler patterns of signals that are interpreted as a unit. Because of an improved method of hybridizing oligonucleotides from samples to microchips, microchips are reusable and transportable. For field study, portable laser or bar code scanners are suitable.

6 Claims, 14 Drawing Sheets

TEMPERATURE IN CENTIGRADE

TEMPERATURE IN CENTIGRADE

OTHER PUBLICATIONS

Chee, M., et al. (1996) "Accessing Genetic Information with High–Density DNA Arrays." *Science* 274: 610–614.

Drobyshev, A., et al. (1997) "Sequence Analysis by Hybridization with Oligonucleotide Microchip: Identification of β–thalassemia Mutations." *Gene,* 188(1): 45–52.

Erlich, H.A. and Bugawan, T.L. (1990) "HLA DNA Typing" *PCR Protocol: A Guide to Methods and Applications,* 261–71. Editor(s): Innis, Michael A., Publisher: Academic, San Diego, CA.

Guschin, D.Y., et al. (1997) "Oligonucleotide Microchips as Genosensors for Determinative and Environmental Studies in Microbiology." *Applied and Environmental Microbiology,* 63(6): 2397–2402.

Shalon, D., et al. (1996) "A DNA Microarray System for Analyzing Complex DNA Samples Using Two–Color Fluorescent Probe Hybridization." *Genome Research,* 6(7): 639–645.

Mirzabekov, A.D. (1994) DNA Sequencing by Hybridization—a Megasequencing Method and a Diagnostic Tool? *TibTech,* 12: 27–32.

Yershov, G., et al. (1996) "DNA Analysis and Diagnostics on Oligonucleotide Microchips." *PNAS* 93: 4913–4918.

Amann, R.I. et al. (1990) "Combination of 16S rRNA–Targeted Oligonucleotide Probes with Flow Cytometry for Analyzing Microbial Populations." Applied and Environmental Microbiology. 56(6): 1919–1925.

Amann, R.I. et al. (1995) "Phylogenetic Identification and In Situ Detection of Individual Microbial Cells without Cultivation."Microbiological Reviews. 59(1): 143–169.

Beattie, K.L. et al. (1995) "Advances in Genosensor Research." Clin. Chem. 41(5): 700–705.

Cantor, C.R. et al. (1992) "Report on the Sequencing by Hybridization Workshop." Genomics. 13: 1378–1383.

Chee, ,M. et al. (1996) "Accessing Genetic Information with High–Density DNA Arrays." Science. 274: 610–614.

Crawford, R.L. (1995) "The Microbiology and Treatment of Nitroaromatic Compounds." Current Opinion in Biotechnology. 6: 329–336.

Day, I.N.M. et al. (1995) "Electrophoresis for Genotyping: Temporal Thermal Gradient Gel Electrophoresis for Profiling of Oligonucleotide Dissociation." Nucleic Acids Research. 23(13): 2402–2412.

Drobyshev, A. et al. (1997) "Sequence Analysis by Hybridization with Oligonucleotide Microchip: Identification of β–thalassemia Mutations" Gene. 199: 45–52.

Dubiley, S. et al. (1997) "Fractionation, Phosphorylation and Ligation on Oligonucleotide Microchips to Enhance Sequencing by Hybridization." Nucleic Acids Research. 25(12): 2259–2265.

Erlich, H.A. and T.L. Bugawan. (1990) "HLA DNA Typing." PCR Protocols: A Guide to Methods and Applications. Academic Press, Inc. 261–271.

Fout, G.S. et al. (1996) "ICR Microbial Laboratory Manual." Environmental Protection Agency Office of Research and Development. EPA/600/R–95/178.

Gherna, R. and C.R. Woese. (1992) "A Partial Phylogenetic Analysis of the 'Flavobacter–Bacteroides' Phylum: Basis for Taxonomic Restructuring." System. Appl. Microbiol. 15: 513–521.

Guo, Z. et al. (1994) "Direct Fluorescence Analysis of Genetic Polymorphisms by Hybridization with Oligonucleotide Arrays on Glass Supports." Nucleic Acids Research. 22(24): 5456–5465.

Guschin, D.Y. et al. (1997) "Oligonucleotide Microchips as Genosensors for Determinative and Environmental Studies in Microbiology." Appl. Environ. Microbiol. 63(6): 2397–2402.

Hacia, J.G. et al. (1996) "Detection of Heterozygous Mutations in BRCA1 Using High Density Oligonucleotide Arrays of Two–Color Fluorescence Analysis." Nature Genetics. 14: 441–447.

Head, I.M. et al. (1993) "The Phylogeny of Autotrophic Ammonia–Oxidizing Bacteria as Determined by Analysis of 16S Ribosomal RNA Gene Sequences." Journal of General Microbiology. 139: 1147–1153.

Ivanov, I.B. et al. (1997) "Identification of Gene Mutations on Oligonucleotide Microchips." Molecular Biology. 31(1): 133–140.

Kemp, P.F. et al. (1993) "Handbook of Methods in Aquatic Microbial Ecology." Lewis Publishers. 1–5.

Khrapko, K.R. et al. (1991) "A Method for DNA Sequencing by Hybridization with Oligonucleotide Matrix." J. DNA Sequencing and Mapping. 1: 375–388.

Khrapko, K.R. et al. (1989) "An Oligonucleotide Hybridization Approach to DNA Sequencing." Febs Letters. 256: 118–122.

Khrapko, K.R. et al. (1991) "Hybridization of DNA with Oligonucleotides Immobilized in Gel: A Convenient Method for Detecting Single Base Substitutions." Moleulyarnaya Biologiya. 25(3): 718–730.

Livshits, M.A. et al. (1994) "Dissociation of Duplexes Formed by Hybridization of DNA with Gel–Immobilized Oligonucleotides." Journal of Biomolecular Structure & Dynamics. 11(4): 783–795.

Maidak, B.L. et al. (1994) "The Ribosomal Database Project." Nucleic Acids Research. 24(17): 3485–3487.

Maskos, U. and E.M. Southern. (1993) "A Novel Method for the Parallel Analysis of Multiple Mutations in Multiple Samples." Nucleic Acids Research. 21(9): 2269–2270.

Mirzabekov, A.D. (1994) "DNA Sequencing by Hybridization—A Megasequencing Method and a Diagnostic Tool?" Tibtech Reviews. 12: 27–32.

Mobarry, B.K. et al. (1996) "Phylogenetic Probes for Analyzing Abundance and Spatial Organization of Nitrifying Bacteria." Appl. Environ. Microbiol. 62(6): 2156–1262.

Nakatsu, C.H. et al. (1995) "The Phylogenetic Distribution of a Transposable Dioxygenase from the Niagara River Watershed." Molecular Ecology. 4: 593–603.

Olsen, G.J. et al. (1992) "The Ribosomal Database Project." Nucleic Acids Research. 20: 2199–2200 (Supplement).

Polsky–Cynkin, R. et al. (1985) "Use of DNA Immobilized on Plastic and Agarose Supports to Detect DNA by Sandwich Hybridization." Clin. Chem. 31(9): 1438–1443.

Pommerening–Roser, A. et al. (1996) "Phylogenetic Diversity within the Genus Nitrosomonas." System. Appl. Microbiol. 19: 344–351.

Sapolsky, R.J. and R.J. Lipshutz. (1996) "Mapping Genomic Library Clones Using Oligonucleotide Arrays." Genomics. 33: 445–456.

Shalon, D. et al. (1996) "A DNA Microarray System for Analyzing Complex DNA Samples Using Two–color Fluorescent Probe Hybridization." Genome Research. 6: 639–645.

Southern, E.M. (1996) "DNA Chips: Analysing Sequence by Hybridization to Oligonucleotides on a Large Scale." TIG. 12(3): 110–115.

Southern, E.M. et al. (1992) "Analyzing and Comparing Nucleic Acid Sequences by Hybridization to Arrays of Oligonucleotides: Evaluation Using Experimental Models." Genomics. 13: 1008–1017.

Stahl, D.A. (1995) "Application of Phylogenetically Based Hybridization Probes to Microbial Ecology." Molecular Ecology: 4: 535–542.

Standard Methods for the Examination of Water and Wastewater. (1995) American Public Health Association. Washington, DC.

Swaminathan, B. (1995) "Diagnostics and Subtyping of Foodborne Pathogenic Bacteria: Objectives for the Year 2000." Molecular Approaches to Food Safety.

Syvanen, A.C. (1999) "From Gels to Chips: 'Minisequencing' Primer Extension for Analysis of Point Mutations and Single Nucleotide Polymorphisms." Human Mutation. 13: 1–10.

Syvanen, A.C. et al. (1990) "A Primer–Guided Nucleotide Incorporation Assay in the Genotyping of Apolipoprotein E." Genomics. 8: 684–692.

Vandamme, P. et al. (1996) "Polyphasic Taxonomy, a Consensus Approach to Bacterial Systematics." Microbiological Reviews. 60(2): 407–438.

Wang, D.G. et al. (1998) "Large–Scale Identification, Mapping, and Genotyping of Single–Nucleotide Polymorphisms in the Human Genome." Science. 280: 1077–1082.

Winzeler, E.A. et al. (1998) "Direct Allelic Variation Scanning of the Yeast Genome." Science. 281: 1194–1197.

Woese, C.R. et al. (1990) "Towards a Natural System of Organisms: Proposal for the Domains Archaea, Bacteria, and Eucarya." Proc. Natl. Acad. Sci. 87: 4576–4579.

Yershov, G. et al. (1996) "DNA Analysis and Diagnostics on Oligonucleotide Microchips." Proc. Natl. Acad. Sci. 93: 4913–4918.

* cited by examiner a. IVS (N)      5'-TMR-CCTGGGCAGGTTGGTATCA-3'(SEQ ID NO:48);
b. IVS I/2 T/A  5'-TMR-CCTGGGCAGGaTGGTATCA-3'(SEQ ID NO:49);
c. IVS I/1 G/A  5'-TMR-CCTGGGCAGaTTGGTATCA-3'(SEQ ID NO:50);
d. IVS I/6 T/C  5'-TMR-CCTGGGCAGGTTGtTATCA-3'(SEQ ID NO:51);
e. IVS I/5 G/T  5'-TMR-CCTGGGCAGGTTGtTATCA-3'(SEQ ID NO:52);
f. CD26   (N)   5'-TMR-GTTGGTGGTGAGGCCCTGG-3'(SEQ ID NO:53);
g. CD26 G/A     5'-TMR-GTTGGTGGTaAGGCCCTGG-3'(SEQ ID NO:54);

Fig. 6

5'-AGGCAACGTG   (1)(SEQ ID NO: 55);
5'-AGGCGACGTG   (2)(SEQ ID NO: 56);
5'-GGTGAACTGG   (3)(SEQ ID NO: 57);
5'-TAAATCTGCG   (4)(SEQ ID NO: 58);
5'-AGGCAACATG   (5)(SEQ ID NO: 59);
5'-CAAAACCTCC   (6)(SEQ ID NO: 60);
5'-GCAAACACCA   (7)(SEQ ID NO: 61);
5'-TACACCATAA   (8)(SEQ ID NO: 62);
5'-ACTGCTCATC   (9)(SEQ ID NO: 63);
5'-CAATGTCTTC  (10)(SEQ ID NO: 64);
5'-CTCCTCATCT  (11)(SEQ ID NO: 65);
5'-TGCCGGTCAA  (12)(SEQ ID NO: 66);
5'-TTAGGACAGC  (13)(SEQ ID NO: 67);
5'-ACACCACAAG  (14)(SEQ ID NO: 68);
5'-CACAATGCCT  (15)(SEQ ID NO: 69);
5'-CAGCAGTAGA  (16)(SEQ ID NO: 70);
5'-TGCGGGTCAA  (17)(SEQ ID NO: 71);
5'-TTAGCACAGC  (18)(SEQ ID NO: 72);

Fig. 9

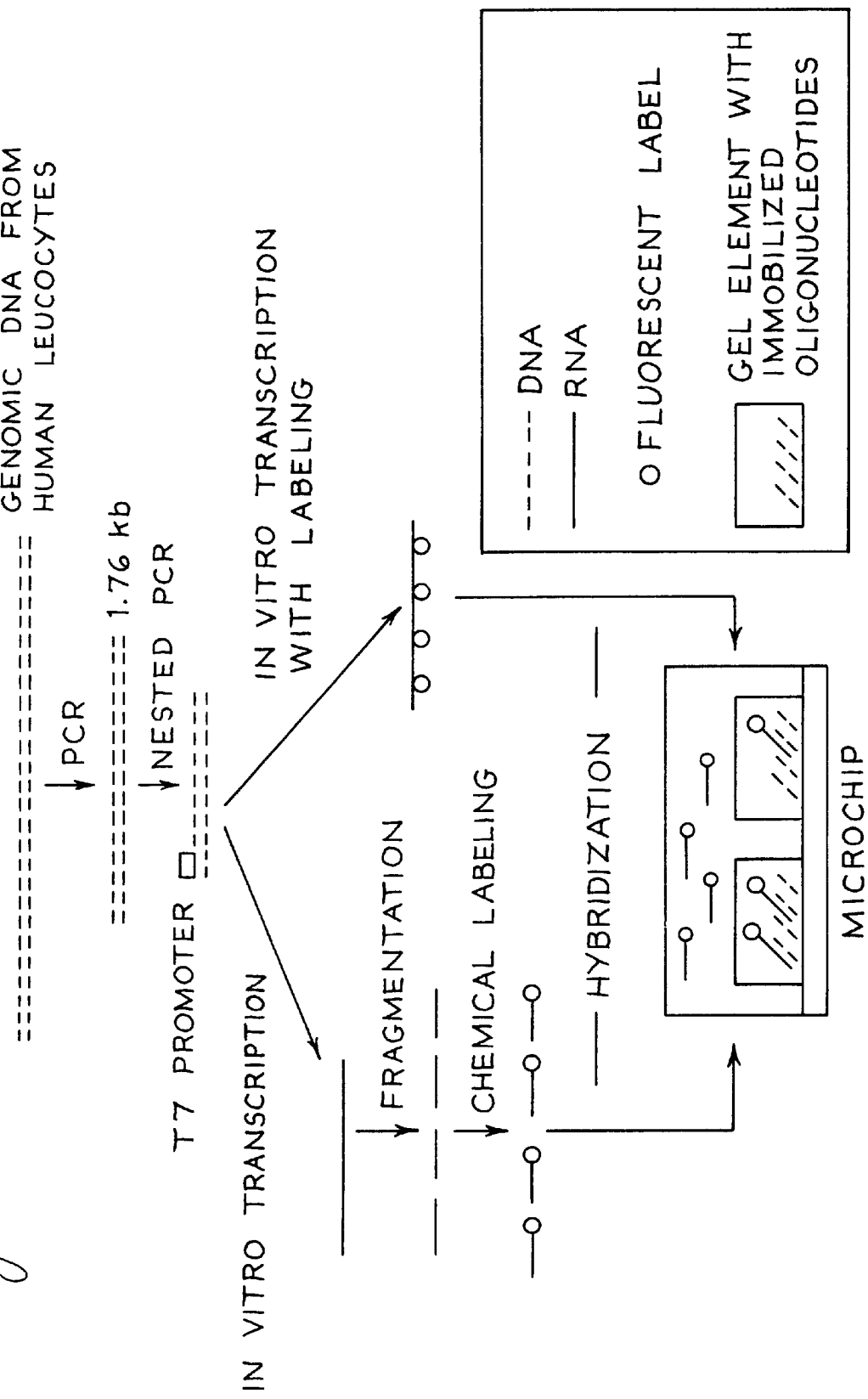

| | | 5'-3' → | |
|---|---|---|---|
| 1 | GAA CCA TGC GGT TCA AAA TG | | positive for B. Anthracis |
| 2 | GC ACC ATG GGG TGC AAA ATG | | negative for B. Anthracis |
| 3 | TC TAG GGT TGT CAG AGG ATG | | positive for B. Anthracis |
| 4 | TC TAG GGT TTT CAG AGG ATG | | negative for B. Anthracis |

FIG. 13

SEQUENCE LISTING

```
<160> NUMBER OF SEQ ID NOS: 78

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: A sample
      (element)-CD26(N-normal)

<400> SEQUENCE: 1
ggcctcacca                                                           10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: B sample
      (element)-CD26(G/A-mutant)

<400> SEQUENCE: 2
ggccttacca                                                           10

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:
      S-D-Bact-0011-a-S-17

<400> SEQUENCE: 3
gtttgatcct ggctcag                                                   17

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      S-D-Bact-1492-a-A-21

<400> SEQUENCE: 4
acggytacct tgttacgact t                                              21

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Primer
      T7V2L-45
```

```
<400> SEQUENCE: 5
ggaattccta atacgactca ctatagggac accatggtgc acctgactcc              50

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 6
tgcgaccggt catgg                                                    15

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 7
cctgtgctcc atgctccg                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 8
cccctctgct gcactcta                                                 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 9
cgatcccctg cttttctc                                                 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 10
cgcgattgta ttacgtgtga                                               20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 11
```

```
tattagcaca tctttcgat                                                19
```

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 12

```
ccgtgaccgt ttcgttcc                                                 18
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 13

```
gctgcctccc gtagggat                                                 18
```

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 14

```
actcctacgg gaggcagc                                                 18
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 15

```
gacgggcggt gtgtacaa                                                 18
```

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Reverse
      primer T7-V2L-103

<400> SEQUENCE: 16

```
ggaattccta atacgactca ctatagggag gtgaacgtgg atgaagttgg              50
```

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17

```
tctccttaaa cctgtcttgt aacc                                          24
```

```
<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
ggagccaggg ctgggcataa aagt                                          24

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
attttcccaa ggtttgaact agctc                                         25

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 20
ataccaacct                                                          10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 21
ataccaatct                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 22
ataccaaact                                                          10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 23
ataccatcct                                                          10

<210> SEQ ID NO 24
```

<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 24
ataccagcct                                                          10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 25
ataccaccct                                                          10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 26
atatcaacct                                                          10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 27
atagcaacct                                                          10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 28
ataacaacct                                                          10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 29
atgccaacct                                                          10

<210> SEQ ID NO 30
<211> LENGTH: 10

```
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 30
ggcctcacca                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 31
ggccttacca                                                              10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 32
tgataccaac                                                              10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 33
tgataccacc                                                              10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 34
gataccaacc                                                              10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 35
gataccaccc                                                              10

<210> SEQ ID NO 36
<211> LENGTH: 10
<212> TYPE: DNA
```

```
<213> ORGANISM: Artificial Sequence
<220> FEATURE:
<223> OTHER INFORMATION: Description of Artificial Sequence: Customized
      oligonucleotide

<400> SEQUENCE: 36
ataccaacct                                                              10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 37
ataccaccct                                                              10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 38
taccaacctg                                                              10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 39
taccaccctg                                                              10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 40
accaacctgc                                                              10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 41
accaccctgc                                                              10

<210> SEQ ID NO 42
<211> LENGTH: 10
<212> TYPE: DNA
<213> ORGANISM: Artificial Sequence
```

<220> FEATURE:
<223> OTHER INFORMATION: Description of Artificial Sequence: Customized
oligonucleotide

<400> SEQUENCE: 42
ccaacctgcc                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Customized
oligonucleotide

<400> SEQUENCE: 43
ccaccctgcc                                                              10

<210> SEQ ID NO 44
<211> LENGTH: 9
<212> TYPE: DNA
<213> ORGANISM: Artificial Sequence
<220> FEATURE:
<223> OTHER INFORMATION: Description of Artificial Sequence: Customized
oligonucleotide

<400> SEQUENCE: 44 caacctgcc                                                               9

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Customized
oligonucleotide

<400> SEQUENCE: 45
caccctgccc                                                              10

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Customized
oligonucleotide

<400> SEQUENCE: 46
aacctgccca                                                              10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Customized
oligonucleotide

<400> SEQUENCE: 47
accctgccca                                                              10

<210> SEQ ID NO 48
<211> LENGTH: 19
<212> TYPE: DNA
<213> ORGANISM: Artificial Sequence
<220> FEATURE:

<223> OTHER INFORMATION: Description of Artificial Sequence: Customized
      oligonucleotide

<400> SEQUENCE: 48
cctgggcagg ttggtatca                                                19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 49
cctgggcagg atggtatca                                                19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 50
cctgggcaga ttggtatca                                                19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 51
cctgggcagg ttgctatca                                                19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 52
cctgggcagg ttgttatca                                                19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 53
gttggtggtg aggccctgg                                                19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Customized oligonucleotide

<400> SEQUENCE: 54
gttggtggta aggccctgg                                                  19

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 55
aggcaacgtg                                                            10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 56
aggcgacgtg                                                            10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 57
ggtgaactgg                                                            10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 58
taaatctgcg                                                            10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 59
aggcaacatg                                                            10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 60
caaaacctcc                                                                           10

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 61
gcaaacacca                                                                           10

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 62
tacaccataa                                                                           10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 63
actgctcatc                                                                           10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 64
caatgtcttc                                                                           10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 65
ctcctcatct                                                                           10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide -continued

<400> SEQUENCE: 66
tgccggtcaa                                                            10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 67
ttaggacagc                                                            10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 68
acaccacaag                                                            10

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 69
cacaatgcct                                                            10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 70
cagcagtaga                                                            10

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 71
tgcgggtcaa                                                            10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Customized
      oligonucleotide

<400> SEQUENCE: 72
ttagcacagc                                                    10

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 73
atggtgtaaa cttgtaccag t                                       21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 74
ttggtagcag cggtagagtt g                                       21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gaaccatgcg gttcaaaatg                                         20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gcaccatggg gtgcaaaatg                                         20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tctagggttg tcagaggatg                                         20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tctagggttt tcagaggatg                                         20

CUSTOMIZED OLIGONUCLEOTIDE MICROCHIPS THAT CONVERT MULTIPLE GENETIC INFORMATION TO SIMPLE PATTERNS, ARE PORTABLE AND REUSABLE

This is a continuation-in-part of copending U.S. patent application Ser. No. 08/780,026 filed Dec. 23, 1996 now abandoned.

The U.S. Government has rights to the invention pursuant to Contract W-31-109-ENG between the U.S. Department of Energy and the University of Chicago representing (Argonne National Laboratory).

A novel microchip is customized to answer specific questions and has oligonucleotides positioned on the microchip so that multiple bits of information are evidenced to a simpler pattern A new method of hybridization to a microchip is also presented.

BACKGROUND OF THE INVENTION

Differences in nucleotide and amino acid sequences may be exploited to analyze environmental, food or biological samples. Detection and identification of microorganisms is important for clinical purposes and for determination of contaminated food, air, water or soil. Studies in environmental microbiology are often limited by the inability to unambiguously identify and directly quantify the enormous diversity of natural populations. This problem is now changing with increasing use of molecular techniques to directly measure different genetic features. (Mobarry et al., 1996; Stahl, 1995; Wagner et al., 1995) For example, DNA probes are now commonly used to detect by hybridization, genes encoding proteins involved in specific catabolic functions, and to resolve different genetic populations in the environment. In particular, the use of group-specific DNA probes complementary to the small subunit (SSU) 16S rRNA has provided a comprehensive framework for studies of microbial population structure in complex systems. Sequencing of this subunit revolutionized microbial classification and led to the discovery of archebacteria. (Woese, 1987) A large number of the sequences for different organisms has been collected. (Maidak et al., 1996) Every microorganism species is characterized by a specific DNA sequence within a variable region of its ribosomal RNA gene or other genes. A highly efficient procedure for microorganism classification and for construction of their evolutionary trees is based on these observations. Identification of specific sequences in ribosomal DNA is a reliable microbial analysis that can be carried out by direct DNA sequencing. However DNA sequencing is a rather complicated, expensive and time consuming procedure to use for serial microbial analysis on a commercial scale for environmental or medical applications. Consequently, new methods are needed to make sequence matching commercially feasible.

Also, methods are needed that are transportable to the field. A nucleic acid hybridization is a highly specific and sensitive procedure that allows a specific sequence to be detected and identified among other millions of sequences in a genome of higher organisms, or among a mixture of different organisms. The principle of hybridization is that sequences hybridize as a function of the similarity of their linear nucleotide sequence. The hybridization of DNA or RNA extracted from even a very complicated mixture to a specific oligonucleotide probe has resulted in unambiguous identification of specific microorganisms in an environmental sample, for example. In the course of such an analysis, RNA or DNA is extracted from a sample of microorganisms isolated from water solutions, air or soil, immobilized on a filter and then hybridized successively with several oligonucleotide probes for different microorganisms. However, for this purpose, the sample needs to be checked for the presence of hundreds or thousands of different oligonucleotides corresponding to various microorganisms which is prohibitively laborious and expensive using present methods and yields results that must be interpreted by a computer in order to decipher the identification. What is needed is a simplified pattern to provide rapid answers to specific questions, e.g. are any known pathogens in a water sample?

The scope of applications of nucleotide hybridization is often limited by the nature of the assays, generally involving the independent hybridization and interpretation of multiple environmental samples to multiple DNA probes. In addition, some detection assays require amplification of the target nucleic acid, for example, via PCR. This may contribute to quantitative biases. Thus, there is need for assays that provide for greater sample through-put capacity and greater sensitivity, rapid read-out of results.

Another area in which specific DNA or RNA sequences are of interest is mutation and polymorphism analyses. The number of base changes discovered (mutations) in different genes is growing rapidly. These changes are associated with genetic diseases, with disease predispositions and cancers, with development of drug resistance in microorganisms, and with genetic polymorphisms. Polymorphisms are useful for determining the source of a sample, e.g. in forensic analyses. Polymorphisms such as in the HLA system are essential to predict success of tissue transplants. The ability to simultaneously analyze many mutations in a gene in a simple, fast, and inexpensive way is essential in clinical medicine and this need has stimulated the development of different methods for screening mutations, but all have serious limitations. What is needed are kits that are transportable and interpretable, e.g. for use in clinics without high technology microscopes.

Hybridization of filter-immobilized DNA with allele-specific oligonucleotides was suggested as a way to screen for mutations. (Conner et al., 1983) However, the number of alleles that can be assayed at one time is limited, the filters are usable only for a few times, and there is little opportunity for complex analysis or easy interpretation of results.

A possible solution to large scale hybridization is to use microchips for DNA sequence hybridizations (SHOM, sequencing by hybridization with oligonucleotides in a microchip) (e.g. Khrapko, 1996; Yershov, 1996). The development of an array of hundreds or thousands of immobilized oligonucleotides, the so-called "oligonucleotide chips", permits simultaneous analysis of many mutations (for a review, see Mirzabekov, 1994). Such arrays can be manufactured by a parallel synthesis of oligonucleotides (Southern et al., 1992; Fodor et al., 1991; Pease et al., 1994; Matson et al., 1995) or by chemical immobilization of presynthesized oligonucleotides (Khrapko et al., 1991; Lamture et al., 1994; Ghu et al., 1994). Glass surfaces (Southern et al., 1992; Fodor et al., 1991; Ghu et al., 1994), glass pores (Beattie et al., 1995), polypropylene sheets (Matson et al., 1995), and gel pads (Khrapko et al., 1991; Yershov et al., 1996) have been used as solid supports for oligonucleotide immobilization. However "Oligonucleotide array technology has not yet lived up to its promise." Southern, 1996 p. 115.

Some of the deficiencies in the art are unpredictability of the results, lack of knowledge of optimum conditions, and failure to demonstrate accuracy and commercial feasibility. Moreover, analysis of the results of hybridization requires computer programs capable of assimilating and interpreting multiples bits of information, and high technology microscopes. The microchips are neither portable, reusable, nor easily interpreted.

SUMMARY OF THE INVENTION

This invention embodies applications of oligonucleotide microchip technology wherein the microchip is a biosensor and customized oligonucleotide microchips are designed for specific applications of nucleic acid hybridization.

Hybridization is a process by which, under defined reaction conditions, partially or completely complementary nucleic acids are allowed to join in an antiparallel fashion to form specific and stable hydrogen bonds.

Aspects of the invention include:
1. microchips designed so that multiple bits of genetic information are converted to a pattern, which is interpreted as a unit, wherein the appearance of the pattern provides answers to specific questions; this construction facilitates providing easily interpretable answers provided by hybridization patterns and removes some need for high technology instruments to interpret the results of hybridization; and
2. improved methods of hybridizing oligonucleotides in a sample to oligonucleotides on a customized microchip do not require a washing step but rather measure non-equilibrium melting curves (temperature curves) that do not require washing with a solution that removes immobilized oligonucleotides from microchips; this means that microchips are reusable because the oligonucleotides anchored within the gel elements, do not wash away, and are available for reuse. (Microchips with samples are generally kept in solution, however, microchips can be dried and stored for many months before being reused.)

The patterns exhibited after hybridization to a microchip generally are not directly related to the nature of the hybridizations and are not simply converting a "yes" or a "no" signal, or a "positive" or "negative" signal to a binary outcome, nor are the patterns of the present invention converting a gradation of quantities to another form of gradation, e.g. colorimetric gradations. The deliberate organization of the oligonucleotides on the microchips themselves does not transmit information; only after hybridization with a test nucleic acid will the hybridization signal itself form the pattern. The pattern is then detected by a detection means which can include visual interpretation without the aid of additional detection instrumentation.

By choosing ordered schemes of oligonucleotide positioning on the microchips, visual signals are simplified and enhanced, e.g. the letter "P" is observed if certain pathogenic groups are present; columns of gel elements on the chip that include the same oligonucleotide probes, will be readily detectable as a positive linear column, if the matching oligonucleotides are in the test sample. The visual appearance may be strong enough to see with the naked eye, may be determined with a UPC (Universal Product Code or "bar code") laser scanner, or with a laser gun. The wavelength of the scanner and the sensor that accepts the signal for a bar code must be concordant with the dye or label used to hybridize the DNA.

Of course, aspects one and two do not have to be used together. Designs that result from converting multiple amounts of genetic information obtained by large numbers of hybridizations of oligonucleotides to simpler, readily interpretable patterns, could be done on microchips constructed and analyzed by the methods used prior to the present invention.

Similarly, the improved methods of providing hybridization results on microchips could be used on microchips that are not designed to convert multiple pieces of genetic information into a simpler pattern.

Other aspects of the invention include improved predictability, increased accuracy, and standardized factors for detection and identification of nucleotide sequences. The improvements result from optimizing conditions, methods and compositions for microchip hybridization. Deliberate ordered schemes that are designed to answer specific questions and that convert complex data to simpler patterns, are followed so that much hybridization information can be readily obtained from a single scan of a microchip to detect hybridization of immobilized oligonucleotides by nucleic acids in a sample to be investigated. Samples include air, water, soil, blood, cells, tissue, tissue culture and a food. An aspect of the invention is that the same microchip can be used for hybridization for more than 20–30 times, without any noticeable deterioration of the hybridization signal because immobilized oligonucleotides are not washed out or stripped. Customized sets of microchips are obtained for specific applications. Also, parallel hybridization of nucleic acids in a sample to many oligonucleotides on a microchip is possible, allowing replication and standardization. For example, the sequence diversity of SSU rRNAs recovered from different microbial populations of varying abundances is analyzed by a single hybridization to a microchip. A large number of HLA alleles, are assayed by a single hybridization to a microchip.

The invention relates a method for identifying a nucleotide sequence in a sample using a microchip, said method comprising:
  a) providing a customized matrix of oligonucleotides on the microchip designed to identify genetic sequences in the sample, wherein an ordered scheme positions oligonucleotides to provide a pattern to answer specific questions after hybridization;
  b) hybridizing nucleic acids extracted from the sample as such or after amplification on said microchip; and
  c) identifying the nucleotide sequences represented in said sample by analyzing the pattern of the oligonucleotides which hybridized to the sequences, said pattern provided by signals.

The nucleic acids suitable for the practice of the invention include DNA, mRNA, 16S rRNA sequences and other RNA species.

Customized oligonucleotide microchips are aspects of the invention. The microchip includes a gel-matrix affixed to a support, said matrix is formed by a plurality of gel pad element sites. The number of sites is determined by the number of oligonucleotides in the array. Each gel element contains one chemically immobilized oligonucleotide of a desired sequence, length and concentration; the gel elements being separated from one another by hydrophobic glass spaces and the gel portions having a vertical height above the plane of the interstitial spaces of generally not more than 30 $\mu$m. In some applications, the same type of oligonucleotides may be immobilized to different gel pads to form a pattern.

The invention relates screening nucleic acid preparations for genes, RNA transcripts or any other unique nucleotide sequences, for example those that encode microbial 16S ribosomal RNAs. Ratios of DNA/RNA or any other unique nucleotide sequences specific for certain types of organisms are suitable. Multiple labeling allows simultaneous detection and quantitative comparison of different nucleic acid sequences that are hybridized to a microchip.

The methods of the present invention include labeling the oligonucleotide sequence in said sample before bringing it in contact with the array. A suitable label is a fluorescent dye. A plurality of different dyes may be used concurrently. Oligonucleotides immobilized on a customized microchip include those complementary to the beta globin gene, sequences specific for Salmonella, or polymorphic HLA allele sequences.

An oligonucleotide microchip for the detection and classification of nitrifying bacteria has a customized design wherein identifying labels in the cells of the microchip refer to oligonucleotides selected from a class of bacteria, and the selection is designed to answer specific questions regarding classification.

An embodiment of an application of the present invention is detecting and identifying microorganisms in samples obtained from the environment, e.g. water, air or soil samples to check for pollutants; biological samples obtained for medical diagnosis; or food samples to check for contamination. Other applications include forensic testing to identify DNA in samples obtained for criminal investigations, and detection of chromosomal fragments, or single gene mutations e.g. for diagnosing genetic diseases such as β-thalassemia or types of cancers. Tissue typing for polymorphic HLA alleles for transplantation or studying human diversity is facilitated.

The nucleic acid preparations are made from samples collected in any type of environment, where detection and identification of the microorganisms in that environment is of interest, or where it is likely that new (previously unidentified) organisms may be discovered.

DNA and RNA molecules in a sample can be separated from each other during their isolation and labeled with different fluorescent dyes. These RNA and DNA molecules are simultaneously hybridized with oligonucleotides on a microchip that is specific to the sample to be tested. The quantitative monitoring of the simultaneous hybridization of differently labeled DNA and RNA with a microscope that can discriminate multicolors at several wave lengths allows the calculation of DNA/RNA ratios in the sample. For bacterial samples, this ratio determines the state of vitality and physiological activity of the bacterium. In an embodiment, the ratio of RNA/DNA is used to discriminate the dead bacterium cells and spores from the active state of microbial growth. In the same way, a DNA or RNA molecule of a bacterial strain stained with one dye can be added in a calculated amount as an internal standard to a sequence or sequences under investigation in which the sequences being investigated stained with a different (second) dye. The fluorescence measurements of hybridization intensities at different wave lengths for the standard and investigated sequences (probes) allow relative quantitative ratios to be determined.

Hybridization on microchips allows unambiguous typing of different groups of chosen bacteria in a sample. Microchip hybridization is a simple, fast, inexpensive and reliable method for bacterial typing.

An aspect of the invention is that there is no limitation on the number of sequences that can be checked or the number of types of microorganisms that can be detected. Instead of multiple sequential hybridizations with different probes of, e.g. a 16S rRNA preparation, only one round of hybridization is required to find out what different sequences are in a sample. The volume of hybridizations is dramatically reduced and the assay requires much less RNA or DNA compared with standard techniques. An advantage is that culturing of bacteria and gene amplification can be avoided.

Methods of the invention significantly reduce sample preparation time, avoid the culturing of organisms collected from field situations, and allow the identification of all species of microorganisms contained in a particular sample. Portable microchips are available for field work.

For example, oligonucleotides complementary to small subunit rRNA sequences of selected microbial groups, encompassing key genera of nitrifying bacteria, were shown to selectively retain or hybridize with labeled target nucleic acid derived from either DNA or RNA forms of the target sequences. Methods and compositions of the present invention discriminate among the Genera, Nitrosomonas, Nitrobacter and Nitrosovibrio sp. using fluorescently labeled nucleic acid probes that hybridize to 16S rRNA sequences. Each species has specific DNA sequences within the variable region of its rRNA genes. Since the rRNAs are naturally amplified, often present in thousand of copies per cell, they provide greater sensitivity, eliminating the need for amplification in many applications.

The invention facilitates identification of organisms from environmental samples in a faster, and more economical approach than presently available. In addition, new species may be discovered that would be highly informative regarding taxonomic status of known as well as newly discovered organisms.

A diagnostic assay of the present invention for a mutation in a gene, includes the following steps:
  a. designing a customized oligonucleotide microchip biosensor comprising oligonucleotides that hybridize to a gene having the mutation, wherein the oligonucleotides are positioned on the microchips so that patterns result depending on what oligonucleotides are in the sample to answer a specific question(s);
  b. contacting a nucleic acid sample to the customized oligonucleotide microchip biosensor under conditions that allow hybridization of the nucleic acid to the microchip; and
  c. determining the pattern of hybridization from which observation the presence of specific nucleic acid sequences is inferred and the specific question is answered.

For diagnostic assays for genetic diseases, sequence analysis of DNA is carried out by hybridization of PCR amplified DNA or its RNA transcripts with oligonucleotide array microchips. Polyacrylamide gel pads containing allele-specific immobilized oligonucleotides are fixed on a glass slide of the microchip. The RNA transcripts of PCR-amplified genomic DNA are optionally fluorescently labeled by enzymatic or chemical methods and hybridized with the microchip. In the field, the chemical methods are preferred because results are obtained faster, and some chemicals will fragment DNA at the same time which is needed for the sample.

When melting curve experiments are performed, both matching and mismatching oligos can be immobilized in the gel pads, and both matching and mismatching nucleic acids can be in the sample. The biochips are reusable in two types of embodiments: 1) the sample or test nucleic acids can be removed or stripped off the chip and a different test sample can be introduced and 2) the same melting point curve experiments can be run and re-run without any washing.

When experiments are performed with a different test sample, the original sample is removed from the chip by a washing or stripping procedure using distilled water at 60° C. with an hour (or up to overnight) incubation. If the melting curve experiments are repeated (or reused) then the same sample is left in contact with the chip and appearance and disappearance of hybridization signal is observed over a variety of temperatures, usually ranging from 0°–50° C.

When the chips are incubated, in order to remove the sample nucleotides, virtually none of the immobilized oligos are removed in the process. This is because the oligos are covalently linked to the gel matrix of the gel pads that form the microchip.

Repeated reuse of the chips in which different samples are applied after sequential removal is usually limited to about 50 uses, because eventually the amount of non-specific or background hybridization signal is greater than one-tenth of a mismatch hybridization signal. The conditions under which a chip would not be reusable (up to 50 times) are very few. Such conditions include allowing the chips to be cooled to −20° C. or performing experiments where the chips are heated to above 70° C., conditions that have been shown to cause degradation of the chips, thus rendering them unstable.

The simultaneous measurement in real time of the hybridization and melting curves on the entire oligonucleotide array is carried out with a fluorescence microscope with a laser light source equipped with CCD camera or a special laser scanner. Some work only with dried microchips. The monitoring of the hybridization specificity for duplexes with different stabilities and AT content is enhanced by its measurement at optimal discrimination temperatures on melting curves. Microchip diagnostics are optimized by choosing the proper allele-specific oligonucleotides from among the set of overlapping oligomers. The accuracy of mutation detection can be increased by simultaneous hybridization of the microchip with at least two differently labeled samples of normal and mutated alleles, and by parallel monitoring their hybridization with a multi-wavelength fluorescence microscope. The efficiency and reliability of the sequence analysis was demonstrated by diagnosing β-thalassemia mutations and HLA polymorphisms. Determining levels of gene expression is an aspect of the invention.

Because the methods of the present invention require only a simple procedure of hybridization and because only one round of hybridization is necessary, it is fast and inexpensive. Because the invention allows a lot of information to be obtained from one experiment, in a simple pattern as compared to the analysis of hundreds of data points, it has increased efficiency. The invention is reliable because the microchips are reusable. Immobilized oligonucleotides are not washed out. There is no waste of hybridization probes, therefore the microchip hybridization is inexpensive and non-isotopic detection simplifies all procedures.

Effective and precise sequence analysis by the hybridization of a probe with rather short microchip-immobilized oligonucleotides depends on many factors. Major factors are the reliability of the discrimination of perfect duplexes from duplexes containing mismatches, differences in stability of AT- and GC-rich duplexes, the efficiency of the hybridization, and simplicity in the preparation of the labeled samples for hybridization.

Identification of base variations is significantly improved by parallel measuring of the melting curves of the duplexes formed on the entire oligonucleotide array, as well as by monitoring the simultaneous hybridization of two differently labeled samples at two wavelengths and by choosing proper allele-specific oligonucleotides.

Other factors to be considered for operation of the invention include (1) regulating the flow of the fluid containing a sample to be tested over the microchip during the hybridization; and (2) control of the temperature of the microchip gel layer and the fluid layer, in a differential manner, by placing a cooling and heating apparatus adjacent to the gel layer and the top fluid layer. The gel layer temperature is controlled in a uniform or gradient manner by a heating/cooling device attached to the glass plate substrate of the gels. For field work, the optimum temperature for a particular question is determined previously in a laboratory.

A definition of "customized microchip" is a microchip of gel elements on a support, wherein the oligonucleotides are immobilized in gel elements according to an ordered scheme such that multiple bits of information are ordered to a simpler pattern to answer a specific question.

Removal of test or sample nucleic acids from microchip is accomplished by an incubation step carried out using distilled water for at least one hour (up to overnight) at 60° C. (This procedure is analogous to the step of "stripping" a filter for re-use in the standard technique of probing a Southern blot.) The immobilized oligonucleotides in the gel matrix are not removed by this incubation as the oligonucleotides are covalently linked to the gel substrate.

BRIEF DESCRIPTION OF THE DRAWINGS

FIG. 6 shows the sequences of β-globin alleles specifying oligonucleotides that were immobilized on a microchip.

FIG. 7 shows the experimental design to detect β-globin mutations using oligonucleotide microchips.

FIG. 9 shows 18 short HLA oligonucleotides.

FIG. 13 illustrates an ordered scheme on a microchip wherein the presence of *B. anthracis*.

DESCRIPTION OF THE PREFERRED EMBODIMENT

Figure 1A:
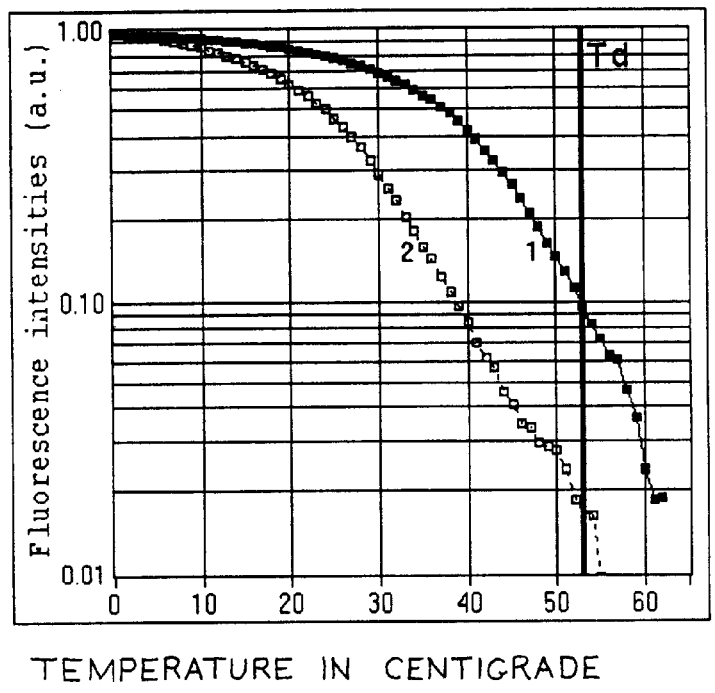
FIGS. 1A & 1B show non-equilibrium melting curves of duplexes of RNA with microchip oligonucleotides.

This invention relates to using customized oligonucleotide microchips as biosensors for the detection and identification of nucleic acids specific for different genes, organisms and individuals in the environment, in food and in biological samples. "Environment" includes water, air and soil. Biological samples include blood, skin, tumors amniotic fluid, tissues, cells and cell cultures. Detection of sequences in nucleic acids is used to identify microorganisms in a sample, to diagnose genetic defects or polymorphisms, to detect gene expression and for forensic studies.

Means for detecting a pattern generated by signals from hybridization within individual gel elements in a microchip of the present invention include a laser scanner, e.g. a laser "gun" such as used to scan bar codes, a CCD camera coupled to a fluorescent microscope. In the field, the naked eye or a scanner is used.

The invention relates to a deliberate and informative arrangement of oligonucleotides immobilized on a microchip, such that upon hybridization with oligonucleotides in a test sample, a pattern is produced that can be interpreted with a suitable means. Hybridization may be detected by letter (FIG. 12), design or bar code pattern (FIG. 13) wherein columns "1" and "3" are dark bars signifying the presence of a pathogen, and the specific pathogen in "1" is a different anthrax species from that in "3." By immobilizing all of one type of oligonucleotide in a column, for example, the pattern is readily detected as a linear column, as contrasted to detecting hybridization in a single small gel element or elements, which requires a microscope to detect it, and computer programs to analyze it.

A nucleic acid hybridization is a highly specific and sensitive procedure and allows a specific sequence to be detected and identified among other millions of sequences in a genome of an organism. However, nucleic acid hybridization is a useful but quite a cumbersome procedure. This drawback can be overcome by using oligonucleotide microchips as biosensors for different microorganisms. Within a small area of a few square millimeters or centimeters, hundreds and thousands of synthetic oligonucleotide probes are immobilized that are specific to ribosomal DNA or to other specific nucleic acids. Subsequent hybridization of a DNA or RNA molecule to the microchip enables a menu of oligonucleotides to be identified in a sample. Instead of having to interpret hundreds or thousands of individual hybridizations, a relative simple pattern produced by hybridizations is analyzed.

For bacterial assays, pure culture microorganisms, purified target nucleic acid or even synthetic oligonucleotides are useful as internal standards, serving to estimate the efficiency of nucleic acid isolation or the absolute amount of target nucleic acid recovered.

The customized oligonucleotide microchips are produced by chemical immobilization of presynthesized oligonucleotides, or by direct synthesis of oligonucleotides on a microchip. If a microchip contains rather long oligonucleotides, the former methods are the methods of choice because before immobilization, the oligonucleotides are purified and checked for their quality.

Methods and technologies have been developed for microchip manufacturing, hybridization of fluorescently labeled DNA and RNA with the microchips and monitoring the hybridization with a fluorescence microscope equipped with CCD-camera, computer and proper software (see U.S. Pat. No. 5,552,270 herein incorporated by reference).

The oligonucleotide microchips consist of many polyacrylamide gel pad elements generally of the size of 40×40×20 μm and larger. The elements are chemically fixed on a glass surface. Each microchip gel element contains a specific presynthesized oligonucleotide that is immobilized through a covalent bond. Hundreds of microchips containing hundreds and thousands of different immobilized oligonucleotides can be manufactured by a specially devised robot. The gel array also offers several advantages over formats using an in situ synthesis of the oligonucleotide array. The synthetic oligonucleotides are purified by gel electrophoresis or HPLC prior to immobilization on the microchip. This provides for stringent quality control of oligonucleotide purity and insures high specificity. The polyacrylamide gel support has a capacity of immobilized oligonucleotides from 0.03 pmol up to 10 pmol per 100×100×20 μm gel pad. This offers improved quantification and better discrimination between perfect and mismatched duplexes. It also provides a way to normalize differences in hybridization signal intensities.

Oligonucleotide microchip technology for sequencing by hybridization is available to identify the presence of microorganisms in a sample of any type, or to find new species. As shown in the examples herein, the hybridization of DNA or RNA extracted from even a very complicated mixture to a specific oligonucleotide probe has resulted in unambiguous identification of microorganisms. The nucleotide sequence of the microorganisms for genes encoding a small subunit of ribosomal 16S rRNA forms the basis for a microchip biosensor. Instead of direct sequencing of the gene, hybridization analysis of DNA or RNA samples with oligonucleotides specific for the microorganisms is performed. This new technology provides efficient microbial analysis and environmental monitoring. Fluorescently labeled DNA and RNA samples from microorganisms are hybridized with microchips containing oligonucleotides specific for several microorganisms. These microorganisms are reliably identified by microchip hybridization patterns. Microorganism biosensor technology is developed, reusable customized microbial oligonucleotide microchips are produced by methods of the present invention, and methods are developed for simultaneous quantitative and qualitative microchip analysis of hundreds and thousands of microorganisms in a sample and for discovery of new ones.

EXAMPLES

The following examples are presented as illustrations of aspects of the invention, rather than limitations of the invention. Other applications include detection of genetic mutations such as are characteristic of hemoglobin disorders; detection of genetic polymorphisms such as HLA; investigation of gene expression; detection of causative agents of diseases; forensic studies; and detection of microbial pollutants.

Example 1

Preparation of an Oligonucleotide Microchip Biosensor

Oligonucleotides are synthesized using a 394 DNA/RNA synthesizer (Applied Biosystems). The synthesis of oligonucleotides for immobilization began with 3-methyluridine at the 3'-terminal position.

In one embodiment, fluorescently labeled RNA was prepared using T7 RNA polymerase. Template DNA (133 and 75 bp long) for in vitro transcription was prepared by PCR amplification with the nested primers T7-V2L-45, 5'-GGAATTCCTAATACGACTCACTATAGGGAC[C] ACC-ATGGTGCACCTGACTCC-3' (SEQ ID NO: 5), as well as with the common reverse primer T7-V2L-103 5'-GGAATTCCTAATACGACTCACTATAGGGAGGT GAACGTGGATGAAGTTGG-3' (SEQ ID NO: 16) AND 5'-TCTCCTTAAACCTGTCTTGTAACC-3' (SEQ ID NO:17). Templates were purified using a QIAquick PCR purification kit (QIAGENE) according to the manufacturer's protocol. The RNA polymerase reaction was performed using the MEGAshortscript™ T7 kit (Ambion) with fluorescein 12-UTP (Molecular probes). Fluorescently labeled ssDNA (single stranded DNA) fragments were prepared by single primer reamplification.

A polyacrylamide gel micromatrix was prepared by photopolymerization of a solution of 4% acrylamide (acrylamide/bisacrylamide 19/1), 40% glycerol, 0.0002% methylene blue, and 0.012% TEMED in 0.1 M sodium-phosphate buffer, pH 7.0. The mixture was applied to an assembled polymerization chamber illuminated with U.V. light.

Two types of microchip matrices (micromatrices) were routinely prepared with gel pad elements of about 60×60×20 $\mu$m and 100×100×20 $\mu$m that were spaced by 120 and 220 $\mu$m, respectively. About 1 nl of activated oligonucleotide solution was transferred to a gel element using either a robot or a simple manual device.

The device includes a Peltier thermostated pin placed under a binocular lens in conjunction with a micromanipulated holder, a power supply, and a refrigerated circulator.

The manufacture of microchips of gel-immobilized oligonucleotides basically consists of three steps; shaping the desired topology of oligo-nucleotides on a gel micromatrix; loading microvolumes of oligonucleotide solutions onto the micromatrix, and immobilizing within the gel oligonucleotides containing the active 3' or 5' terminal aldehyde or amine groups.

To avoid the exchange of different oligonucleotide solutions applied on adjacent gel pads, the pads are separated on the micromatrix by a hydrophobic glass surface. Two-dimensional scribing or laser evaporation is used for micromatrix preparation, but these procedures require rather complex equipment and experienced personnel. The photopolymerization method significantly simplifies the procedure and makes it accessible to a biochemical laboratory.

Microfabrication by mask-directed photopolymerization (e.g., a photoresist method in microelectronics) is a well developed technique. From several acrylamide photopolymerization techniques tested, modified—methylene—blue induced photo-polymerization produced the best results for micromatrix manufacture. The gel matrix consists of gel pads photopolymerized on a glass slide. The gel pads are formed according to the mask topology due to the lack of photopolymerization in places covered by a nontransparent grid.

The microchip is manufactured by applying the activated oligonucleotide solutions onto the micromatrix of gel elements containing active hydrazide or aldehyde groups. A simple device exists for manual loading of up to 100 different oligonucleotides on a micromatrix. The transfer is carried out by the hydrophilic upper surface of a pin that is first immersed into, and is wetted with, an oligonucleotide solution, and then is withdrawn from the solution and brought into contact with the gel surface. This transfers about 1 nl of oligonucleotide solution with a reproducibility of ±10%. The temperature of the pin is maintained near the dew point of the ambient air to avoid the evaporation of this microvolume solution in the course of transfer.

The oligonucleotides are positioned according to a design wherein hybridization pattern data will be reduced to a readily interpretable pattern.

Example 2

The Hybridization of Microchips with DNA and RNA using a Hybridization Buffer

Fluorescently labeled DNA or RNA (5 $\mu$l, 0.1–1 pmol/$\mu$l were hybridized to a microchip at +5° C. in a hybridization buffer containing 1 M NaCl, 1 mM EDTA, 1% Tween-20, and 10 mM sodium phosphate at a pH of 7.0, for between about 2–24 h. The microchip was covered with a cover glass or a Teflon sheet so that a 300-$\mu$m space is above. Then the hybridization solution containing DNA or RNA fragments was substituted with 10 $\mu$l of cooled hybridization buffer. The microchip with the cover glass was placed on a thermostabilized table. Hybridization was monitored quantitatively using a specially constructed multicolor epifluorescent microscope with a 4×4 mm observation field equipped with a CCD camera and suitable software.

Example 3

Analysis of Melting Curves; a Hybridization Buffer is Not Required

The polyacrylamide gel used on a microchip provides more than 100 times higher capacity for three-dimensional immobilization of oligonucleotides than does a two-dimensional glass surface. The high concentration of immobilized oligonucleotides facilitates the discrimination of mismatched duplexes and enhances the sensitivity of measurements on the microchips. This allows the use of a CCD-camera-equipped fluorescence microscope (Yershov et al., 1996) although it is less sensitive than laser scanning systems (Lipshutz et al., 1995), but offers the advantage of monitoring the hybridization on a microchip at different temperatures in real time for measurement of the melting curves. Melting curves are defined herein as produced by plotting the amount of duplexes [fluorescent intensity] versus temperature. The procedure, the software, and the hybridization microchamber (Yershov et al., 1996) have all been developed for recording melting curves at a wide range of temperatures simultaneously for perfect and mismatched duplexes formed upon hybridization of a probe with all microchip oligonucleotides.

A significant amount of time is needed for the microchips hybridized with rather long RNA or DNA probes to achieve equilibrium. Therefore, non-equilibrium dissociation melting curves were measured. However, they are not far away from equilibrium where some difference in heating rate did not significantly affect the results. The melting curves for hybridization of, for example, synthetic 19-mers with the microchip oligonucleotides reached equilibrium under the same conditions that were used for measuring non-equilibrium RNA and DNA melting curves. The melting curves can also be measured after a few minutes, far away from equilibrium, if an internal standard is added to a tested sample. This standard can be a differently labeled RNA of a normal allele. This significantly speeds up the identification of nucleic acid base changes.

Example 4

Choice of Optimum Melting Temperatures for Non-Equilibrium Hybridization

This invention embodies an improvement in the SHOM technology in which hybridizations between an array of gel-immobilized nucleotides (a microchip) and the unknown nucleotides to be tested are measured at optimal, discriminatory melting temperatures. This improvement is achieved by parallel measuring of the melting curves of the duplexes formed by hybridization on the entire oligonucleotide array, as well as by monitoring the simultaneous hybridization of two samples of nucleotides labeled with different fluorochromes, and judicious choice of proper allele-specific oligonucleotides as the immobilized probes. The fluorochromes chosen for the labeling emit light of sufficiently differing wavelengths, that both types of labels can be measured in the same reaction mixture.

The greatest discrimination between perfect and mismatched duplexes was achieved at a temperature at which the intensity of the hybridization signal from a perfect duplex dropped to one-tenth of its initial value; at such a temperature, the hybridization intensities from mismatched duplexes usually approached the background level. The temperature at which the initial signal of hybridization drops by a factor of 10 is termed the discrimination temperature (Td.).

The dissociation curves for perfect and mismatched duplexes are parallel at the range of about 10° (in the middle of the curves) when plotted on a semilogarithmic scale. At this 10° C. range, the ratios of the signals for perfect and mismatched duplexes remain rather constant. This makes the discrimination procedure robust to some inaccuracies in determining Td. The discrimination temperature depends on experimental conditions (rate of heating, ionic strength, probe concentration, extent of fragmentation, and so forth) which can vary from one experiment to another. However, these variations affect Td and the relative intensities of the hybridization signals to a similar extend for all microchip elements and therefore do not significantly distort the discriminations. Therefore, to provide a reference Td, the oligonucleotides CD26(N) and CD 26 G/A, which form perfect and mismatched duplexes, respectively, with all RNAs tested, were introduced into the microchip.

Since Td is robust to some inaccuracy in measurements, 19-mer oligodeoxynucleotides were used in these experiments instead of more expensive 19-mer oligoribonucleotides. There are differences in the stability of DNA-DNA homoduplexes relative to DNA-RNA heteroduplexes (Lesnik and Freier, 1995). The pattern of hybridization of the microchip with RNA derived from patients and with 19-mers was rather similar to that from the 10-mers. Hybridization with corresponding synthetic oligonucleotides is preferred as a control when a mutation is identified in an RNA sample by its hybridization with a diagnostic microchip.

A mixture of fluorescently labeled RNA samples was prepared from two patients; the first sample was TMP-labeled RNA from a patient that is homozygous for the normal CD26 area of the beta-globin allele; the second sample is fluorescein-labeled RNA from a patient that is heterozygous for the normal CD26 area and a mutation CD26 G/A alleles. This mixture was hybridized with a microchip consisting of two microchip elements that contained the following immobilized oligonucleotides:

```
                                    SEQUENCE

A sample (element)-CD26 (N-normal)   5'-GGCCTCACCA-3MeU-3'   (SEQ ID NO:1)

B sample (element)-CD26 (G/A-mutant) 5'-GGCCTTACCA-3MeU-3'   (SEQ ID NO: 2)
```

Figure 1B:
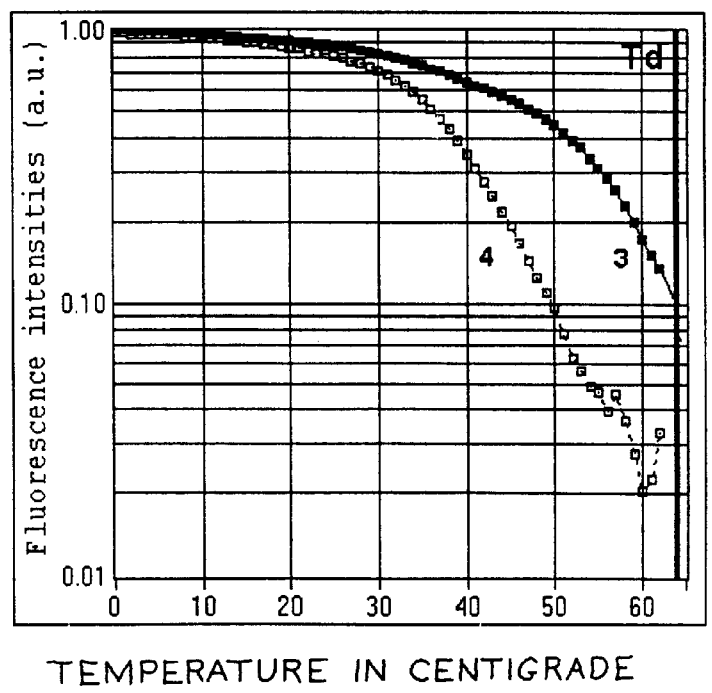

In the case of beta-thalassemia mutation detections described in Example 6 herein: (1) RNA transcripts of PCR-amplified DNA were hybridized with immobilized oligonucleotides; (2) the Td values for perfect 40% and 70% GC-rich duplexes were 52° and 64°, respectively; (curves 1 and 3 in FIGS. 1A and 1B); (3) the immobilized oligonucleotides were chosen from among a set of overlapping sequences; and (4) the two samples included in the reaction mixture were a mutated allele RNA labeled with one fluorochrome and a sample of the normal allele RNA labeled with a different fluorochrome.

The Td is determined by hybridization with an RNA sample if an allelic DNA is available. If such DNA is unavailable, the Td can be measured from the hybridization data resulting from experiments performed with synthetic oligonucleotides corresponding to the mutated allele of interest.

Figure 2:
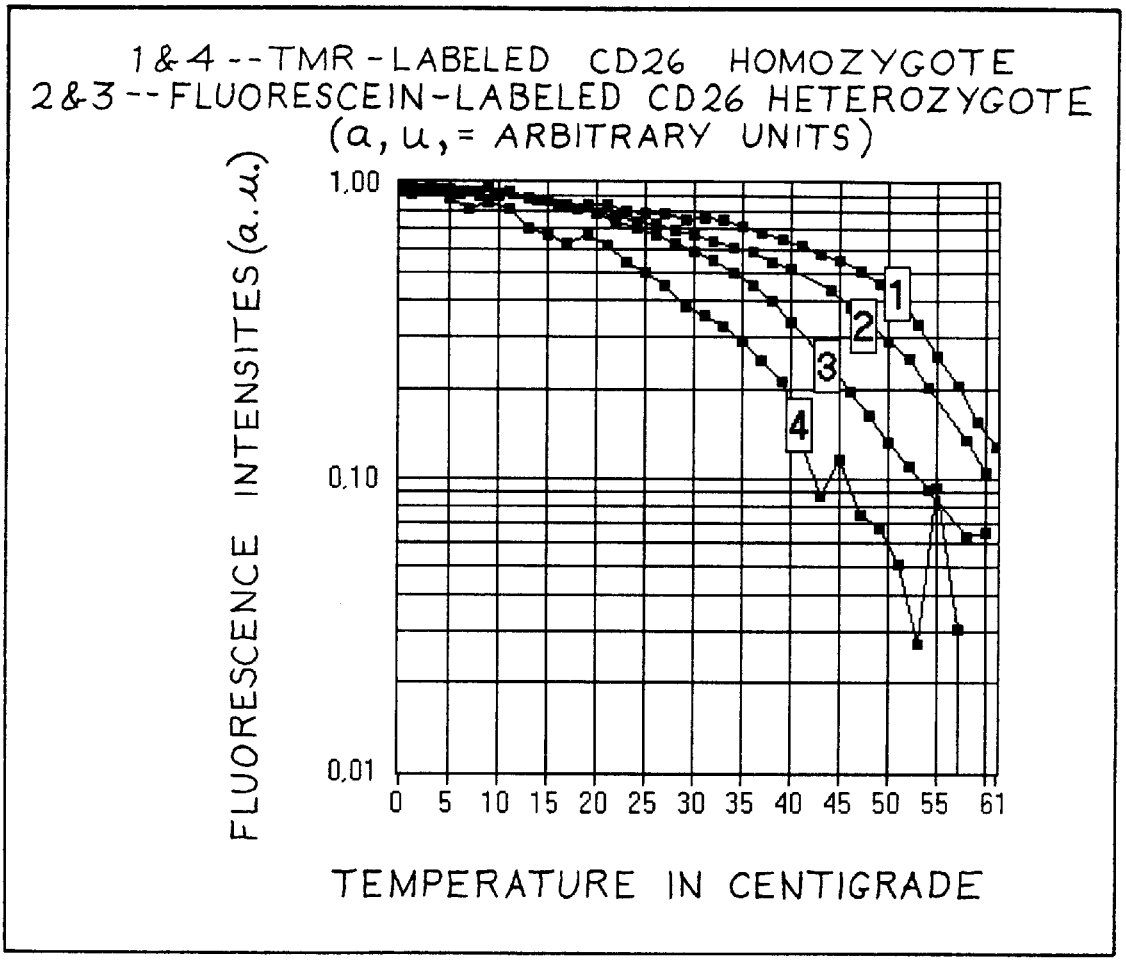
FIG. 2 shows an example of four melting curves for 75-nt-long RNA fragments hybridized with the microchip oligonucleotides. The RNA was derived from a patient having the IVS I/2 T/A mutation in the β-globin gene. The curves were normalized to the initial hybridization signals. Melting curves 1 and 3 correspond to perfect duplexes; curves 2 and 4 correspond to duplexes containing internal T-T or G-T mismatches, respectively. The curves for the perfect and mismatched duplexes are shifted by about 10° C. from each other.
Figure 3A:
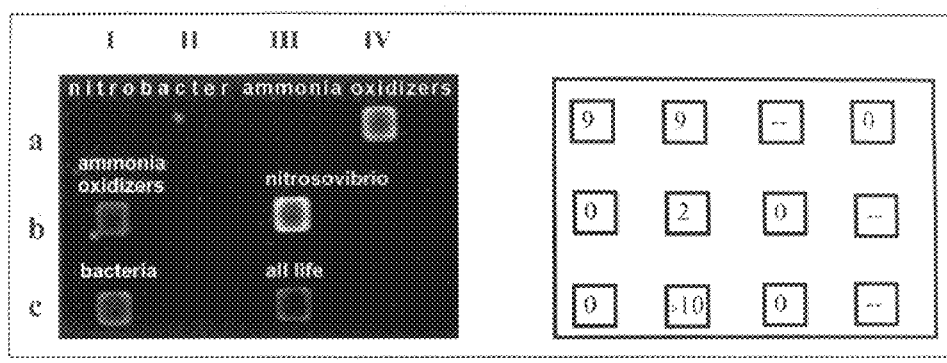
FIGS. 3A–3D show hybridization of fluorescein labelled 16S rRNAs to a microchip. The microchip with immobilized probes (see Table 1 and Table 2) was hybridized sequentially to in vitro transcribed 16S rRNA of Nitrosovibrio tenuis (A), Nitrosomonas europaea (B), E. coli (C), and with E. coli rRNA recovered from isolated ribosomes (D). The panels to the right display the number of mismatches between each probe and the RNA.
Figure 3B:
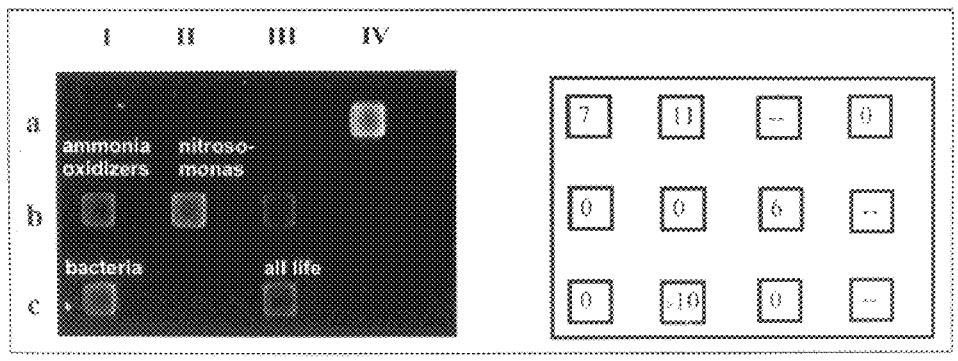
Figure 3C:
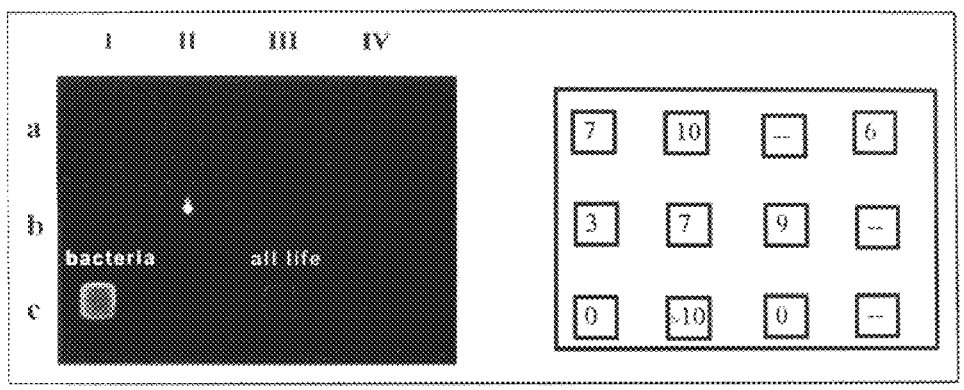
Figure 3D:
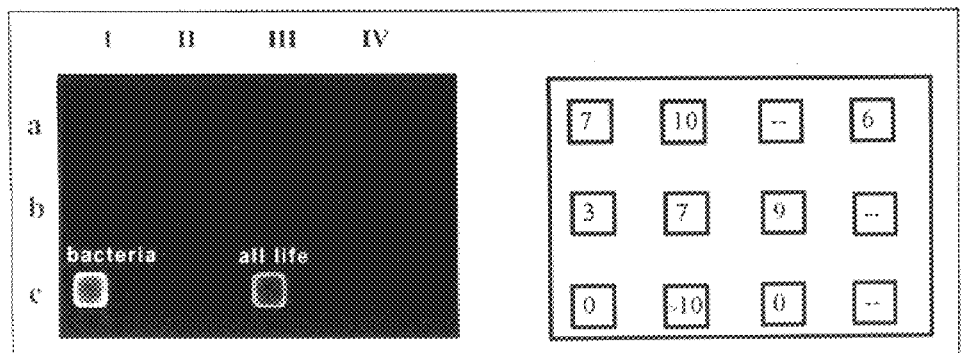

Usage of different filters during the registration of the signal, allowed the independent, simultaneous registration of the sample, which was marked with the different dyes; TMP (red) and fluorescein (green), on the same element of the microchip. FIG. 2 demonstrates 10 the interaction of sample 1, with the A microchip element; Graph 2 demonstrates the interaction of sample 2 with the A microchip element; Graph 3 demonstrates the interaction of sample 2 with the B microchip element; and Graph 4 demonstrates the interaction of sample 1 interaction with the B microchip element.

Example 5

Use of a Customized Microchip Matrix Biosensor to Identify Nitrifying Microorganisms The results in this example were obtained 20 using methods previously available, not the non-equilibrium melting curves. Microorganisms that degrade nitroaromatic compounds include Pseudonomas, Arthrobacter, Nocarida, Myco- bacterium, and fungi.

Previously, methods for detection of these 25 bacteria were tedious and inaccurate. For example, to detect Pseudonomas capable of degrading nitroaromatic compounds, 2-nitroluene was tested as a sole carbon, energy and nitrogen source. It was difficult to isolate the bacteria from soil samples to perform the test.

Nitrifying bacteria have proved particularly difficult to study using cultivation techniques, such as most probable number (MPN) and selective plating because of their long generation times and poor counting efficiencies. Thus, a rapid and non-culture dependent enumeration technique for nitrifiers could greatly facilitate research in their ecology.

Microchips with 100×100×20 μm gel pads (alternatively 60×60×20 μm), fixed on a glass surface and containing a set of 10 oligonucleotides 15–20 bases-long were manufactured for bacterial typing experiments. The set included oligonucleotides complementary to different regions of 16S ribosomal RNA. Since rRNA's are naturally amplified, and often are present in thousands of copies per cell, they provide great sensitivity and eliminate the need for amplification in many applications. One oligonucleotide is represented in most living organisms, another is typical for most of bacteria and the rest belong to nitrosos (nitrifying) bacteria only. The group of nitrosos bacteria oligonucleotides consists of two oligonucleotides typical of nitrobacter, two typical of nitrosomonas and one typical of nitrosovibrio. One oligonucleotide was complementary to an antisense strand of rDNA for hybridization with ribosomal dsDNA, that was PCR amplified from genomic or cDNA.

The following scheme for an ordered oligonucleotide loading (placing on a chip) is useful for bacterial (or organism, species) typing. In the micromatrix design shown in Table 1, the first oligonucleotides characterize the highest order (i.e. to distinguish a living organism). [Uni 1390-CIII]. Reducing the order step by step down to the lowest level, i.e. from family, to genus, to species provides further discrimination of oligonucleotides that are present in a sample being investigated. For example, for oligonucleotides used to classify nitrifying bacteria, a bacterial oligonucleotide would be in the next position. [Bac 338—CI and NonBac338—CII]. Oligonucleotides specific to nitrobacter [Nb1000—AI and NIT3—AII] and ammonia oxidizers [NEU23—AIII, Nso190—AIV and Nso1225—BI] follow in any order. Finally, oligonucleotides specific to Nitrosomonas [Nsm156—BII] and Nitrosovibrio [Nsv443—BIII] complete the micromatrix design.

The microchip was evaluated using three different rRNA preparations (phenol extracts of cellular RNA, RNA isolated from purified ribosomes, and in vitro transcripts of cloned ribosomal DNA), and both fragmented double-stranded and single-stranded DNA. Hybridizations were performed in a formamide buffer at low temperature in order to enhance microchip durability and decrease RNA degradation. Although all DNA and RNA preparations could be used, the best discrimination was observed for in vitro transcribed rRNAs using the hybridization conditions evaluated in this study.

The hybridization of the microbial microchips was carried out with five different preparations of target nucleic acids. Ribosomal RNA and total RNA were recovered from cells. RNA transcribed in vitro as well as single- and double-stranded PCR-amplified 16S rDNA were obtained from plasmids containing the cloned 16S rRNA gene. All of these sample types provided a comparatively reliable identification of the microorganisms by their hybridization with the microchip-immobilized oligonucleotides and could be used for different purposes. For example, the rRNA provides a naturally amplified target. Also, since cellular ribosome content is well known to vary with growth rate, it is generally thought that direct quantification of rRNA serves to identify the more active environmental populations. In contrast, analysis of PCR amplified rDNA provides a more general measure of all microorganisms present in a sample. Alternatively, these measures could be combined. For example, the RNA and DNA components of an environmental sample could be isolated and labelled with different fluorescent dyes. Following their combined hybridization, the resulting ratio of RNA and DNA hybridizing to an individual gel element could be used to infer the physiological status of the corresponding microbial population.

Table 2 shows the sequences of the oligonucleotides and other characteristics of them.

TABLE 1

Micromatrix Design for Nitrifying Microorganisms.

| | I | II | III | IV |
|---|---|---|---|---|
| A | Nb1000 | NIT3 | | Nso190 |
| B | Nso1225 | Nsm156 | Nsv443 | |
| C | Bac338 | NonBac338 | Uni1390 | |

TABLE 2

| Oligo-nucleotide Name and Position | Sequence (5' to 3') | Specificity | Microchip location Table 1 | Td[1] C |
|---|---|---|---|---|
| Nb1000 | 5'-tgc gac cgg tca tgg-3'(SEQ ID NO:6) | Nitrobacter | A-1 | 42° |
| NIT3 | 5' cct gtg ctc cat gct ccg-3'(SEQ ID NO: 7) | Nitrobacter | A-II | 66°[2] |
| NEU23 | 5'-ccc ctc tgc tgc act cta-3'(SEQ ID NO: 8) | Ammonia oxidizers | A-III | 66°[2] |
| NS0190 | 5'-cga tcc cct gct ttt ctc-3'(SEQ ID NO: 9) | Ammonia oxidizers | A-IV | 62° |
| NSO1225 | 5'-cgc gat tgt att acg tgt ga-3'(SEQ ID NO:10) | Ammonia oxidizers | B-I | 51° |
| NSMO156 | 5'-tat tag cac atc ttt cga t-3' ?(SEQ ID NO:11) | Nitrosomonas | B-II | 46° |

TABLE 2-continued

| Oligonucleotide Name and Position | Sequence (5' to 3') | Specificity | Microchip location Table 1 | Td[1] C |
|---|---|---|---|---|
| NSV443 | 5'-ccg tga ccg ttt cgt tcc-3'(SEQ ID NO: 12) | Nitro-sospira-like | B-III | 52° |
| BAC338 | 5'-gct gcc tcc cgt agg gat-3'(SEQ ID NO: 13) | Bacteria | C-I | 54° |
| NonBAC338 | 5-'act cct acg gga ggc agc-3'(SEQ ID NO: 14) | Eub338 complementary strand | C-II | 54° |
| UNI1390 | 5 'gac ggg cgg tgt gta caa-3'(SEQ ID NO: 15) | all life (with a few exceptions) | C-III | 44° |

[1]Experimentally determined.
[2]Estimated from in situ hybridization.

A number of hybridization conditions were tested in terms of efficiency and specificity of hybridization. Hybridization in formamide containing buffer at low temperature gave good results. Hybridizations were performed at 5° centigrade in 33% formamide. RNA samples and covalent bonding of oligonucleotides with the support (hence durability of microchips) are more stable at low temperatures. In addition, these conditions were favorable from a point of view of RNA stability and microchip durability similar to other RNA molecules at low temperatures of about 0°–5° C.

The hybridization on a microbial microchip was carried out with in vitro RNA transcripts of 16S rDNA of different nitroso bacteria, total RNA extracts and ribosomal RNA extracted form E. coli and Desulfovibria vulgurus as well as PCR amplified double or single stranded DNA of 16S rDNA.

The probes for ammonia oxidizing bacteria show different discrimination specificity under different conditions. FIG. 3 shows the fluorescence of individual gel elements on the microchip following hybridization to the 16S rRNAs of Nitrosovibrio tenuis (A), Nitrosomonas europaea (B), and E. coli, either in vitro transcribed (C) or recovered from isolated ribosomes (D). The same microchip was used for each hybridization following washing with distilled water. Each microchip was routinely used for up to 20–30 hybridization experiments. The appropriate pattern of hybridization was observed for all gel elements shown, despite a significant difference in dissociation temperatures ($T_{ds}$) previously determined using membrane support hybridization (Table 1). For hybrids of comparable stability, discrimination is generally achieved by washing at increasing temperatures (described below) or by simultaneously evaluating their melting characteristics, since the fluorescence analyzer can monitor hybridization signals in real time.

Figure 4A:
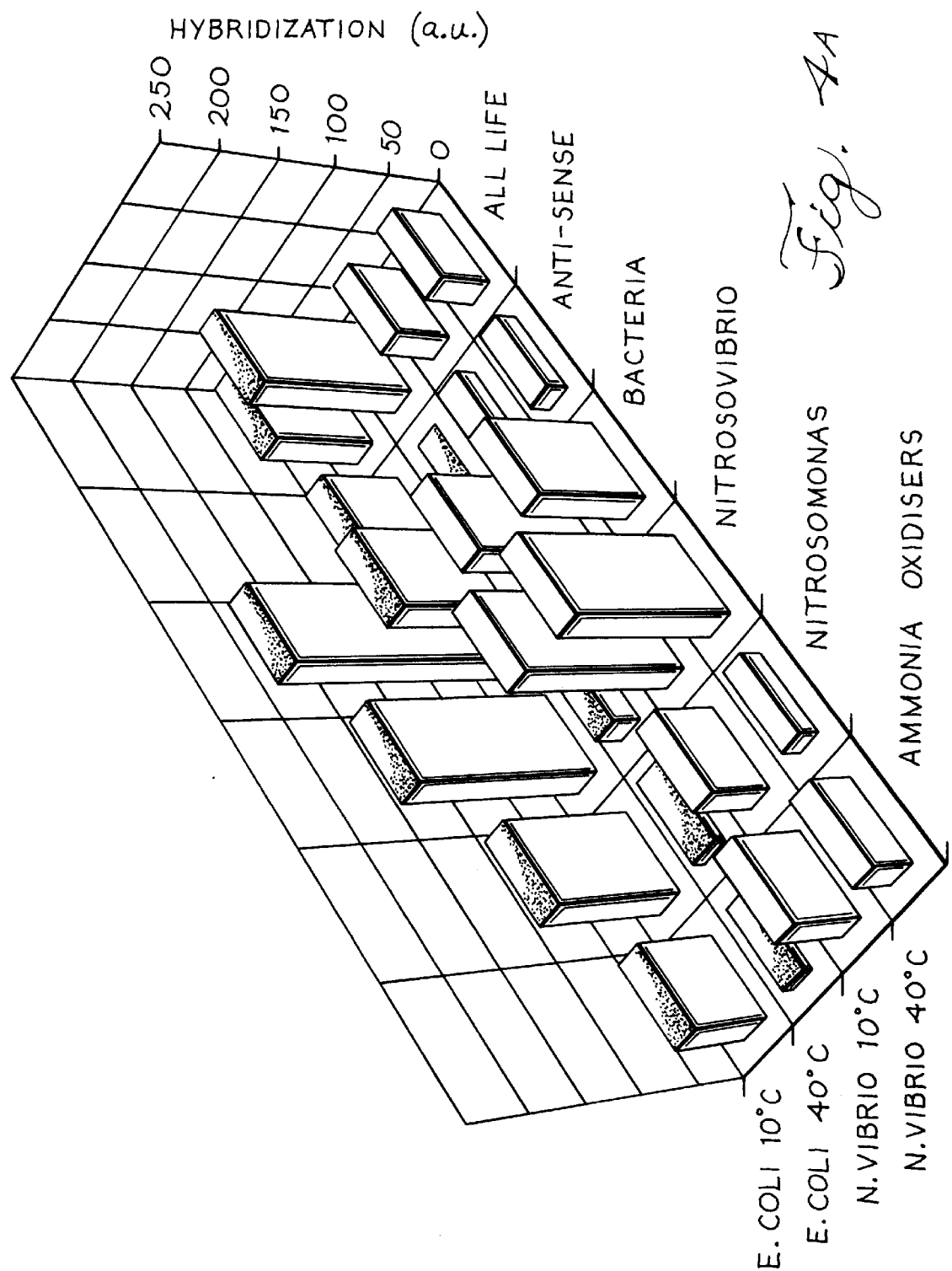
FIGS. 4A and 4B show hybridization of the mixture of differently labelled E. coli and Nitrosovibrio tenuis rRNAs to the microchip at 10° C. and 40° C., measured simultaneously by multicolor detection. A. The microchip was hybridized with a mixture of fluorescein labelled Nitrosovibrio tenuis and tetramethylrhodamine labelled E. coli 16S rRNA and washed serially at the indicated temperatures, arbitrary units of fluorescence intensities. B. The ratio of the hybridization intensities of Nitrosovibrio tenuis ($I_{Nt}$) to E. coli ($I_{E.\ coli}$) 16S RNA measured at 10° C. and 40° C. $R=(INt/I_{E.\ coli})$.
Figure 4B:
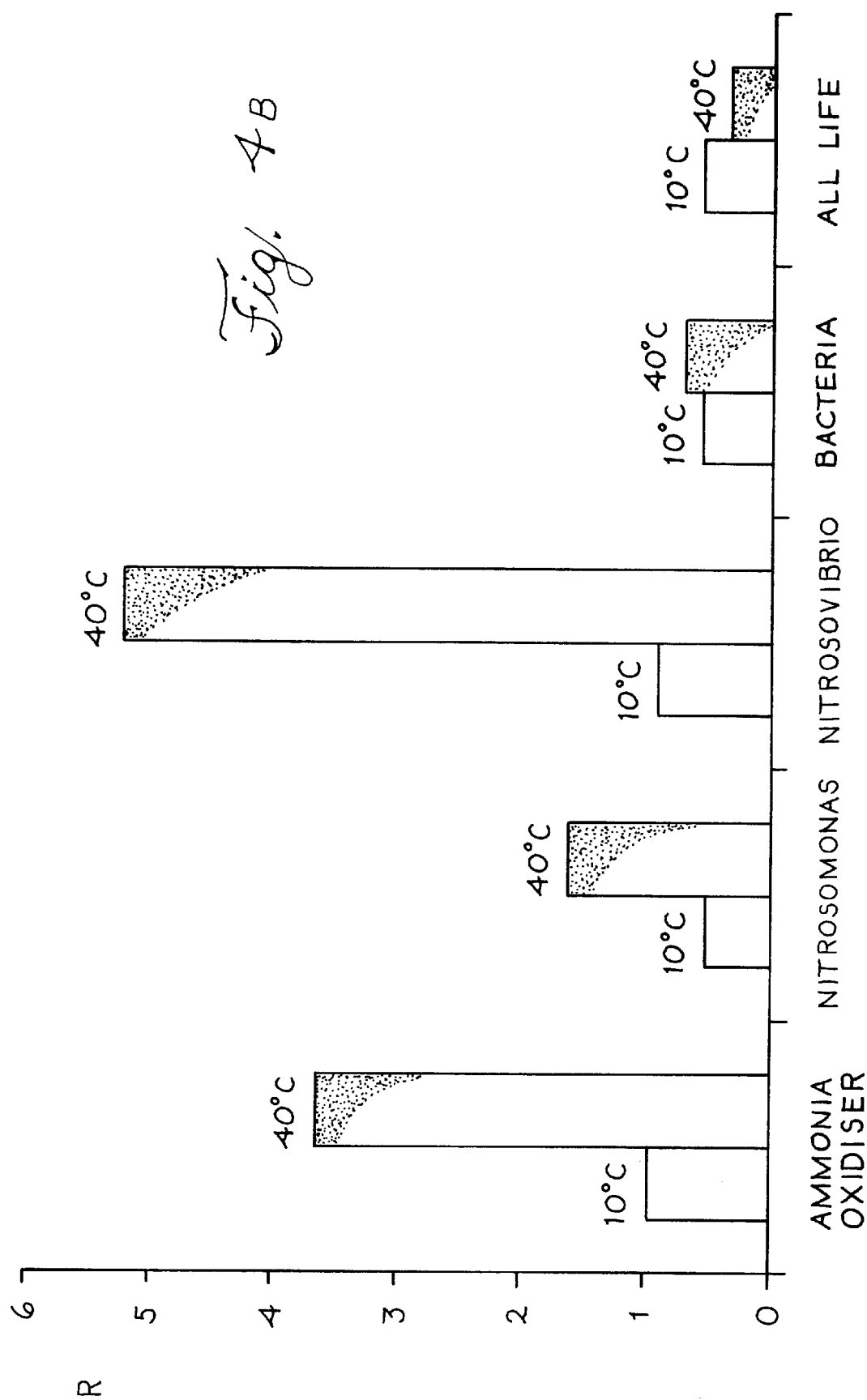

FIGS. 4A and 4B shows the results of an experiment evaluating the effect of increasing washing temperature on target RNA retention. A mixture of Nitrosovibrio tenuis and E. coli 16S rRNA labelled with different fluorescent dyes (fluorescein and tetramethylrhodamine, respectively) was hybridized to the chip at 5° C. The hybridization solution was then replaced with washing buffer and the retention of each RNA species was measured following each 10° C. incremental increase in temperature (up to 60° C.) using multicolor detection. Nonspecific hybridization of E. coli rRNA to Nso1225 (ammonia oxidizer), Nsm156 (nitrosomonas), and NonBac338 (anti-sense) was observed following the 10° C. wash. However, this nonspecific hybridization was significantly reduced following the 40° C. wash. In like manner, the 16S rRNA of Nitrosovibrio tenuis hybridized to Nitrosomonas (Nsm156) at 10° C., but was reduced to near background (compared to NonBac338) following the 40° C. wash. Using the methods of the present invention, hybridization buffer is not required. A more complete correction for differences in stabilities of duplexes can be carried out by measuring the equilibrium or non-equilibrium melting curves for all microchip elements. This would provide a basis to compensate for the various factors influencing individual duplex stability, e.g., their length, GC-content, and competition with secondary and tertiary structures in RNA and DNA.

FIG. 4B shows the ratios of hybridization intensities of fluorescein labelled Nitrosovibrio tenuis to tetramethylrhodamine labelled E. coli. with different microchip oligonucleotides at 10° C. and 40° C. (the ratios are derived from the data presented on FIG. 4A. These ratios were not changed significantly for oligo-nucleotides specific to bacteria and all living organisms between 10° C. and for more stringent conditions at 40° C. However, the ratio is dramatically increased at 40° C. (compared to 10° C.) for oligonucleotides specific to ammonia oxidizers and nitrosovibrio. This increase reflects the greater duplex stability of Nitrosovibrio tenuis RNA with the complementary oligonucleotides compared with E. coli. RNA. Although the nitrosomonas ratio increases, the signal originating from each labelled RNA is near background. This experiment demonstrates that the inclusion of second dye-labelled RNA, either isolated from cells or synthesized, could be used as an internal standard for quantitative assessments of hybridization patterns.

Figure 5:
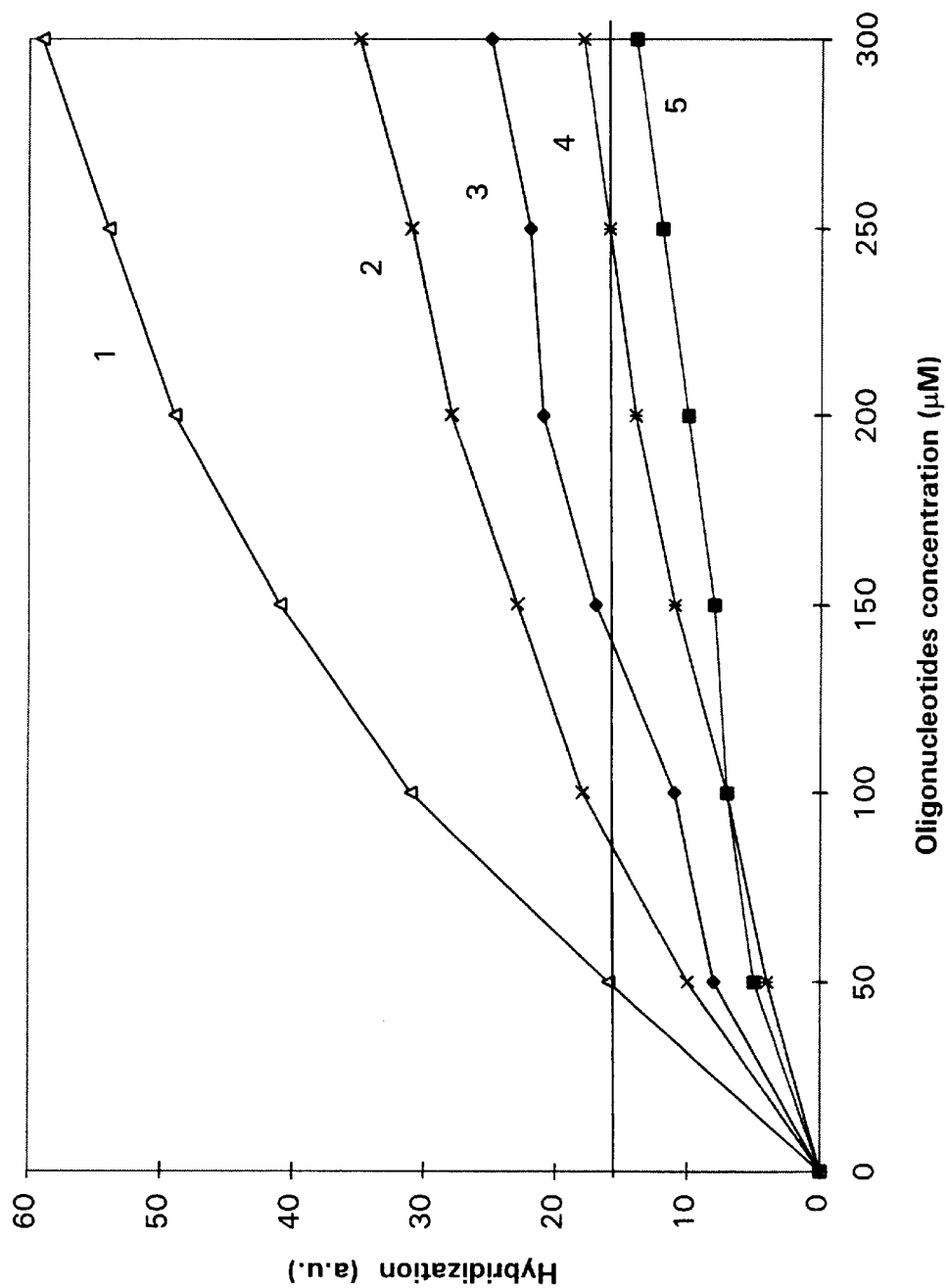
FIG. 5 illustrates the concentration effect of the immobilized oligonucleotides on the hybridization intensities. A microchip with different concentrations of immobilized oligonucleotides was hybridized with N. tenuis 16S rRNA labelled with fluorescein and washed at 20° C. Curve 1 corresponded to Nsv443 (nitrosovibrio-like) probe, curve 2—Bac338 (Bacteria), curve 3—Nso1225 (ammonia oxidizers), curve 4—Uni1390 (all life), and curve 5—Nsm-156 (nitrosomonas), a.u.—arbitrary units of fluorescence intensities.

Variable hybridization to the different gel elements is the expected consequence of using a single hybridization condition to evaluate an array of probes, each having different kinetics of association and dissociation. To some extent these difference can be normalized by varying the concentration of oligonucleotides in the individual gel elements. For example, the relatively low hybridization signals of Nso1225(b-I) and Uni1390 (c-III) compared to Nsv443 (b-III) could each be elevated by increasing the amount of the corresponding oligonucleotides probes immobilized in the gel. This approach was evaluated by synthesizing a microchip with selected probes immobilized at several different concentrations, up to 6 times higher than that used in the experiments previously described. This was accomplished by multiple applications of the standard loading solution (100 pmol/$\mu$l probe) to each gel element. Comparable hybridization of Nso1225 (ammonia oxidizer) and Nsv443 (nitrosovibrio-like) was achieved following three applications of the Nso1225 probe (FIG. 5).

Similarly, two applications of Bac338 (bacteria) and five of Uni1390 (all life) resulted in hybridization comparable to Nsv443.

Strains used. *Escherichia coli, Desulfovibrio vulgaris* strain PT2, *Nitrosovibrio tenuis* strain NV12, *Nitrosomonas europaea* strain ATCC 19718, and Nitrosomonas strain C-56 were used as sources of nucleic acid for these experiments.

RNA preparation. Total cellular RNA was isolated by phenol/chloroform extraction. For some of the samples, a ribosome enrichment was performed before RNA extraction. Forty ml of log phase growth *E. coli* or *D. vulgaris* strain PT2 was centrifuged at 3500 g for 10 min. and resuspended in 4 ml of 4° C. ribosome buffer. Ribosome enrichment buffer consisted of 20 mM $MgCl_2$, 50 mM KCl, 50 mM Tris at pH 7.5, and 5 mM β-mercaptoethanol in diethyl pyrocarbonate treated double-distilled water. The cell suspension was divided between 4 screwtop microfuge tubes and 0.5 g of 0.1 mm $ZrO_2$ beads were added. The cell suspensions were disrupted for 2 min., put on ice for 5 min., and disrupted again for 2 min. The cell suspensions were centrifuged at 14000 g for 10 minutes. The supernatant, which contained the ribosomes, was recovered and transferred to ultracentrifuge tubes. Ribosomes were pelleted by ultracentrifugation in ribosome buffer at 55,000 rpm (201,000 g average) for 50 minutes in a Beckman Optima Series TL swinging bucket rotor (Beckman, Fullerton, Calif.), for a Svedberg sedimentation factor of 70S. After centrifugation, the supernatant was discarded and the RNA was recovered from the pelleted ribosomes by extraction with pH 5.1 phenol/chloroform. Quality and quantity of extracted RNA was evaluated by polyacrylamide gel electrophoresis and ethidium bromide staining.

Cloning of 16S rDNA and in vitro production of RNA transcripts. DNA was extracted from *E. coli, Desulfovibrio vulgaris* PT2, *Nitrosovibrio tenuis* NV12, *Nitrosomonas europaea* 19718, and Nitrosomonas strain C-56 cell pastes using a guanidine/diatom method. Near-complete 16S rDNA genes (ca. 1500 base pairs) were recovered from each by PCR amplification using S-D-Bact-0011-a-S-17 (GTTTGATCCTGGCTCAG)(SEQ ID NO:3) and S-D-Bact-1492-a-A-21 (ACGGYTACCTTGTTACGACTT) (SEQ ID NO:4) as primers and a premixed PCR amplification buffer (Pharmacia Biotech Inc. Piscataway, N.J.), consisting of 0.2 mM Mg++, 2.5 mM each DATP, dCTP, dGTP, dTTP, 0.2 mM of each amplification primer, and 2.5 units of Taq DNA polymerase (Pharmacia). Temperature cycling was done in an Idaho Technology thermocycler (Idaho Falls, Id.) using 30 cycles of 15 sec at 94° C., 20 sec at 50° C., 30 sec at 72° C. The PCR-products were cloned in a pCR plasmid (Invitrogen, San Diego, Calif.) according to manufacturers instructions. Plasmids were isolated using the Wizard kit (Promega, Madison, Wis.) and used for in vitro transcription of the cloned SSU rRNA genes.

DNA oligonucleotide probes. All probes were complementary to the SSU rRNAs and previously characterized using a membrane hybridization format. Fives probes hybridize to different groups of ammoniaoxidizing bacteria within the beta-subdivision of the Proteobacteria. S-G-Nso-190-b-A-19 (Nso190) and S-G-Nso-1225-a-A-20 (Nso1225) encompass all sequenced ammoniaoxidizers of the beta-subclass of Proteobacteria, probe S-G-Nsm-156-a-A-19 (Nsm156) identifies members of the genus Nitrosomonas (also including *Nitrosococcus mobilis*), probe S-G-Nsv-443-a-A-20 (Nsv443) is specific for the Nitrosovibrio/Nitrosolobus/Nitrosospira group, and probe S-G-Nsm-653-a-A-18 (NEU23) is specific for the halotolerant members of Nitrosomonas. Probes for members of genus Nitrobacter (nitrite oxidizing) were S-G-Nit-1000-b-A-15 (Nb1000) and S-G-*Nit*-1035-a-A-18 (NIT3). Other probes used were S-D-Bact-0338-a-A-18 (Bac338) which hybridizes to members of the bacterial domain; S-D-NBac-0338-a-S-18 (NonBac338), complementary to the antisense strand of the Bac338, and S-*-Univ-1390-a-A-18 (Uni1390) complementary to the SSU RNA of nearly all characterized living organisms, with the exception of some protists.

RNA and DNA labeling and fragmentation. Single stranded DNA was prepared by asymmetric PCR according to Ausubel et al. (1994) using a 100 times excess of the forward primer. Briefly, DNA was partially depurinated in 80% formic acid for 30 min. at 20° C., then incubated in 0.5 M ethylenediamine hydrochloride (pH 7.4) for 3 hr at 37° C., followed by 30 min. at 37° C. in the presence of 0.1 M $NaBH_4$. Fluorescein isothiocyanate was incorporated into fragmented DNA by incubation in absolute DMSO at room temperature for 1 hr.

RNA was fragmented by base hydrolysis and dephosphorylated with bovine phosphatase. Fragmented RNA was oxidized by $NaIO_4$ and labeled either by ethylenediamine mediated coupling of 6-carboxyfluorescein (FAM) succinamide or by direct incorporation of tetramethylrhodamine-hydrazide (TMR).

Microchip fabrication. A matrix of glass-immobilized gel elements measuring 60×60×20 or 100×100×20 μm each and spaced apart by 120 or 200 μm respectively was prepared. The polyacrylamide gel was activated by substitution of some amide groups with hydrazide groups by hydrazine-hydrate treatment. oligonucleotides were activated by oxidizing 3'-terminal 3-methyluridine using $NaIO_4$ to produce dialdehyde groups for coupling with hydrazide groups of the gel and coupled to each micromatrix element by applying 0.5–1 nl of the activated oligonucleotide solution (100 pmol/μl) using a specially devised robot.

Hybridization and image analysis. Probe binding was quantified by measuring the fluorescence conferred by the binding of fluorescently labeled DNA or RNA (tetramethyl rhodamine or fluorescein) to the individual gel elements. Hybridization and washing was controlled and monitored using a Peltier thermotable (with a working range of −5.0° C. to +60.0° C.) mounted on the stage of a custom-made epifluorescent microscope. The microchip was hybridized at 5° C., either overnight or for 6 hr, in 2–5 μl of the hybridization buffer [33% formamide, 0.9 M NaCl, 1 mM EDTA, 1% Tween-20, and 50 mM sodium phosphate (pH 7.0)] at a concentration of DNA and RNA between 0.2–2 pmol/μl. The hybridization mixture was replaced with 5–10 μl hybridization buffer without formamide immediately prior to microscopic observation. Exposures were in the range of 0.1–10 sec depending on the signal intensity, but were typically around 1 sec. Fluorescence was monitored either at room temperature or using a range of temperatures between 5–60° C.

Conditions for the coupling of micromolecules to the acrylamide gel were devised to rule out the possibility of liquid evaporation during immobilization and to ensure that covalent bonding of oligonucleotides with the gel matrix proceeds to completion. After the microvolumes of the oligonucleotide solutions have been applied to all cells of the matrix, the micromatrix gel elements were swelled by condensing water from the ambient air. Then the micromatrix surface was covered with a thin layer of an inert nonluminescent oil, and chemical coupling of the activated oligonucleotides to the activated polyacrylamide was carried out to completion.

Example 6

Use of Microchip Biosensors As Diagnostic Assays

The microchip technology was successfully tested for identification of single base changes in genomic DNA and RNA for reliable diagnosis of human genetic diseases. A customized microchip contained oligonucleotides specific to β-thalassemia normal and abnormal β-globin genes. The hybridization with PCR-amplified DNA or RNA samples derived from genomic DNA of subjects allowed unambiguous identification of a mutation in a sample to be tested. Reliability of the identification was enhanced by using simultaneous hybridization with two samples of a normal and mutated RNA stained with different fluorescence dyes and monitoring the hybridization at different wavelengths; by simultaneously measuring the melting curve for duplexes formed on a microchip, and by using a proper set of several oligonucleotides complementary to the mutated site of the DNA.

A number of the most commonly occurring β-thalassemia mutations with β-globin gene were used in diagnostic assays with oligonucleotide microchip biosensors. These mutations were splice-site mutations for the $1^{st}$, $2^{nd}$, $5^{th}$, and $6^{th}$ nucleotides in the first intron (IVS I) of the β-globin gene: IVS I/1 G/A (G/A=substitution of G for A), IVS I/2 T/C, IVS I/5 G/T, IVS I/5 G/C, IVS I/6 T/C, and G/A substitution in the $26^{th}$ codon (GAG) of the first exon (FIG. 6), (also known as abnormal hemoglobin E) (see Diaz-Chico et al., 1988 for terminology).

A microchip with 10OH10OH20 μm gel elements (Yershov et al., 1996) contained immobilized decadeoxyribonucleotides, that is, 10-mers that correspond to normal and mutant β-thalassemia alleles. These 10-mers discriminated mismatches less reliably than 8-mers, but were hybridized more efficiently than 8-mers. 10-mers were, therefore, preferred for this assay. Table 3 shows the sequences of the allele-specific oligonucleotides immobilized on the microchips. It was expected that mismatches within the duplexes would have a much higher destabilization effect than mismatches at the terminal positions (Khrapko et al., 1991); therefore the mutated bases were placed inside of the immobilized oligonucleotides.

Single- and double-stranded PCR-amplified globin DNA fragments of different lengths and collected after a random fragmentation were tested in assays for identification of some of these mutations. However, the hybridization of RNA is preferred over DNA hybridization. RNA fragments were derived from PCR-amplified genomic DNA by transcription with T7 RNA polymerase (Lipshutz et al., 1995). About 100 copies of unlabeled or fluorescently labeled RNA transcripts are synthesized per DNA molecule, providing a convenient way to prepare a sufficient amount of the hybridization probes. RNA is fragmented and one fluorescent dye molecule is introduced per fragment.

Table 3 shows the sequences of the microchip allele specific 10-mers. The oligonucleotides of microchip I are complementary to the coding strand of DNA of the β-globin gene of patients with β-thalassemia single-base mutations (G/A—substitution of A for G) in the $1^{st}$, $2^{nd}$, $5^{th}$, or $6^{th}$ nucleotides of the first intron (IVS I/1, 2, 5, 6) of the β-globin gene and in the codon #-26 (CD-26) of the first exon. Oligonucleotides 1–16 of microchip II correspond to the normal and IVS I/2 G/T allele. The mutated and corresponding normal bases are placed from the $2^{nd}$ to the $9^{th}$ positions of the 10-mers from their 3'-end. The mutated bases are shown in lowercase bold letters and corresponding oligonucleotide bases in the normal allele are underscored. The oligonucleotide synthesis and the microchip manufacturing were described by Yershov et al. (1996).

Microchip I was successively hybridized with RNA 75 and 133 nt long without fragmentation or after fragmentation (133fr, Table 5, probes 3a and 4a) and with 6 synthetic 19-mer oligodeoxyribonucleotides corresponding to β-thalassemia mutations. The RNA and 19-mers were labeled with TMR except for RNA probes 2a, 2b, and 6b, which were labeled with fluorescein (F1). The melting curves (FIGS. 1A–B, FIG. 2) were measured simultaneously for all microchip oligonucleotides at each hybridization. These curves provided values of hybridization intensities at the discrimination temperature, Td. R is the ratio of the hybridization signal of a mismatched duplex (Im) to the signal of the perfect duplex (Ip) estimated at Td in parallel for all microchip oligonucleotides. R=Im/Ip. $d_{19}$-synthetic 19-deoxymers were complementary to allele specific 10-mers immobilized on the microchips.

Table 4 shows the effect of the position of the allelic base within 10-mers on mutation detection. Microchip II contains two sets of 10-mers corresponding to the normal and IVS ½ T/G alleles. The microchip was hybridized with the TMR-labeled normal allele 19-mer and to an RNA 75 nt long. $T_{0.1}$ is the temperature at which the hybridization signals for a microchip duplex drops to ⅒ of its initial value at 0° C. $-0T_{0.1}$ (a perfect duplex) minus $T_{0.1}$ (the corresponding mismatched duplex.)

Fluorescently labeled RNA probes were prepared from a fragment of the β-globin gene from the first exon (Lawn et al., 1980). PCR amplification of a 1.76-kb fragment of the human β-globin gene mapped from nucleotides −47 to +1714 (Lawn et al., 1980) was carried out with mg genomic of DNA (Poncz et al., 1982) and 50 pmol each of the forward primer: 5'-GGAGCCAGGGCTGGGCATAAAAGT-3') (SEQ ID NO:18) (−47→−23) and the reverse primer 5'-ATTTTCCCAAGGTTTGAACTAGCTC-3' (SEQ ID NO:19)(+1689→+1714). (FIG. 7) The amplification was carried out in a DNA thermal cycler (Gene Amp PCR System 2400, Perkin Elmer Corporation in 100 μl of a buffer containing 200 mM each of dATP, dCTP, dGTP, dTTP, 2.5 MM M9Cl₂, 2 units of Taq DNA polymerase (BioMaster, Russia), 50 mM KC1, 10 mM Tris-Hcl, pH 9.0, and 0.1% Triton X-100. The reaction conditions were 30 cycles, with 45 sec at 95° C., 90 sec at 66° C., and 120 sec at 72° C. PCR product was purified from 2% low gel/melting temperature agarose gel (NuSieve agarose, FMC). The 159 bp and 102-bp DNA fragments were amplified with 10 ng of the 1.75 kb DNA with three nested primers, two containing T7 promoter sequence and a common reverse primer. The nested primers were T7-V2L-45. (5'-GGAATTCCTAATACGACTCACTATAGGGA CACCATGGTGCACCTGACTCC-3' (SEQ ID NO: 5)-44→+66); T7-V2L-103 (5'-GGAATTCCTAATACGACTCACTATAGGGAGGTGA ACGTGGATGAAGTTGG-3' (SEQ ID NO:16); +102→−123); and 5'-TCTCCTTAAACCTGTCTTGTAACC-3' (SEQ ID NO:17) (common reverse; 153→+176). The amplification was carried out in 25 cycles (15 sec at 95° C., 30 sec at 62° C., and 30 sec at 72° C.). PCR products were purified by QIAGEN QIAquick PCR Purification Kit. The PCR-amplified 159 or 102 bp DNA (4–5 μg) containing T7 promoter was transcribed with 400 units of T7 RNA polymerase (Promega) to produce 133 and 75 nt long RNA in 80 μl of buffer containing 300 mM HEPES, pH 7.6, 30 mM MgCl₂, 16 mg of BSA, 40 mM DTT, 30 units of Rnasin (Promega) and 4 mM each of ATP, CTP, GTP, and UTP for 3 h at 38° C. Deproteinization of the reaction mixture was carried out in 20 mM EGTA, pH 8.0, 2% SDS, and Proteinase K (10 mg/ml) for 15 min at 37° C. The mixture was extracted first with equal volumes of phenol and then with equal volumes of chloroform, precipitated twice by one volume of isopropyl alcohol, from 0.5 M LiClO$_4$ and dissolved on a Bio-Spin P6 column (BioRad).

Fragmentation of 10–100 μg of RNA to an average length of 20- to 40-mers was carried out in 50 μl of 0.1 M KOH for 30 min. at 40° C. Then 5 μl of 1M HEPES, pH 7.6, and 15 μl of 1% HCO$_4$ were added at 4° C. The pellet of potassium perchlorate was removed by centrifugation and RNA was precipitated by 10 volumes of 2% LiClO$_4$ in acetone. The RNA was washed twice with acetone and dried for 20–30 min. at room temperature. The fragmented RNA was dephosphorylated in 50 μl of 20 mM Tris-HCl, ph 8.0, 1 mM MgCl$_2$, 1 mM ZnCl$_2$, 10 units of Rnasin, 5–7 units of calf intestine phosphatase (CIP) for 1 hour at 37° C. RNA deproteinization and purification was carried out as described herein.

For chemical fluorescence labeling of RNA the 3'-terminal dephosphorylated nucleoside was oxidized in 20 μl of 10 mM sodium periodate for 20 min. at room temperature. RNA was precipitated with acetone. A 10 molar excess of 10 mM TMR-hydrazine in 10% acetonitrile was added to oxidized RNA fragments in 20 μl of 20 mM sodium acetate at pH 4.0.

The reaction mixture was incubated 30–40 min at 37° C., and the hydrazide bond between the RNA and dye was stabilized by reduction with freshly prepared 1.5 μl of 0.2 M NaCNBH$_3$ and incubated for 30 min. at room temperature. Then the mixture was extracted four times with water saturated n-butanol and precipitated with acetone. Alternatively, RNA was labeled by incorporation of fluorescein-UTP during the transcription with Ambion MEGAshortscript kit according to the manual.

The hybridization of fluorescently labeled RNA (1 pmol/μl) with the microchips was carried out at 0° C. for 18 h. In many cases, the intensities of the hybridization signals at 0° C. were similar for perfect and mismatched duplexes. The perfect and mismatched duplexes as well as the duplexes having various GC and AT contents displayed different stabilities and therefore were tested at different temperatures.

Table 4 summarizes the results of hybridization of the diagnostic microchips with 1) RNA probes derived from a number of homozygous and heterozygous β-thalassemia patients; and 2) with corresponding 19-mers. The table shows the Td for perfect duplexes formed on each microchip oligonucleotide. The relative intensities, R, of the hybridization signals for a different microchip oligonucleotides in Table 3 are normalized to the signals for a perfect duplex at the Td (estimated as 1.0). In most cases the ratios for mismatched duplexes are less than 0.1 and close to 0. These values are low enough to allow unambiguous identification of the homozygous and heterozygous mutations in patients at the Td (when the hybridization signals from only perfect duplexes are observed). The hybridization of homozygote RNA (Table 5, probes 1a, 2a, 2b, and 3a) with the microchip shows the distinctive formation of a perfect duplex only with one immobilized oligonucleotide and mismatched duplexes with all others. Two perfect duplexes were unambiguously identified upon hybridization with a heterozygote RNA (Table 5, probe 4a).

TABLE 3

The sequence of the microchip allele specific 10-mers.

| # | Position of mutated Allele | base | Sequence | Location |
|---|---|---|---|---|
| | | | MICROCHIP I | |
| 1 | IVS (N) | — | 5'-A TAC CAA CCT-gel (SEQ ID NO:20) | +141 |
| 2 | IVS I/1 G/A | 8 | 5'A TAC CAA tCT-gel (SEQ ID NO: 21) | +141 |
| 3 | IVS I/1 G/T | 8 | 5'-A TAC CAA aCT-gel (SEQ ID NO: 22) | +141 |
| 4 | IVS I/2 TA | 7 | 5'-A TAC Cat CCT-gel (SEQ ID NO:23) | +141 |
| 5 | IVS ½TC | 7 | 5-A TAC Cag CCT-gel (SEQ ID NO:24) | +141 |
| 6 | IVS I/2 T/G | 7 | G'-A TAC Cac CCT-gel (SEQ ID NO: 25) | +141 |
| 7 | IVS I/5 G/A | 4 | 5'-A TAt CAA CCT-gel (SEQ ID NO: 26) | +141 |
| 8 | IVS I/5 G/C | 4 | 5'-A TAg CAA CCT-gel (SEQ ID NO: 27) | +141 |
| 9 | IVS I/5 G/T | 4 | 5'-A TAa CAA CCT-gel (SEQ ID NO: 28) | +141 |
| 10 | IVS I/6 T/C | 3 | 5'-A TgC CAA CCT-gel (SEQ ID NO: 29) | +141 |
| 11 | CD 26 (N) | — | 5'-G GCC TCA CCA-gel (SEQ ID NO:30) | +125 |
| 12 | CD 26 G/A | 6 | 5'-G GCC TtA CCA-gel (SEQ ID NO:31) | +125 |
| | | | MICROCHIP II | |
| 1 | IVS (N) | 9 | 5'-TGA TAC CAA C-gel (SEQ ID NO:32) | +143 |
| 2 | IVS I/2 T/G | 9 | 5'-TGA TAC CAc C-gel (SEQ ID NO:33) | +143 |
| 3 | IVS (N) | 8 | 5'-GA TAC CAA CC-gel (SEQ ID NO:34) | +142 |
| 4 | IVS I/2 T/G | 8 | 5'-GA TAC CAc CC-gel (SEQ ID NO:35) | +142 |
| 5 | IVS (N) | 7 | 5'-A TAC CAA CCT-gel (SEQ ID NO:36) | +141 |
| 6 | IVS ½T/G | 7 | 5'-A TAC Cac CCT-gel (SEQ ID NO:37) | +141 |
| 7 | IVS (N) | 6 | 5'-TAC CAA CCT G-gel (SEQ ID NO:38) | +140 |
| 8 | IVS I/2 T/G | 6 | 5'-TAC CAc CCT G-gel (SEQ ID NO:39) | +140 |
| 9 | IVS (N) | 5 | 5'-AC CAA CCT GC-gel (SEQ ID NO:40) | +139 |
| 10 | IVS I/2 T/G | 5 | 5'-AC CAc CCT GC-gel (SEQ ID NO:41) | +139 |
| 11 | IVS (N) | 4 | 5'-C CAA CCT GCC-gel (SEQ ID NO:42) | +138 |
| 12 | IVS I/2 T/G | 4 | 5'-C CAc CCT GCC-gel (SEQ ID NO:43) | +138 |
| 13 | IVS (N) | 3 | 5'-CAA CCT GCC-gel (SEQ ID NO: 44) | +137 |
| 14 | IVS I/2 T/G | 3 | 5'-CAc CCT GCC C-gel (SEQ ID NO:45) | +137 |
| 15 | IVS (N) | 2 | 5'-AA CCT GCC CA-gel (SEQ ID NO:46) | +136 |
| 16 | IVS I/2 T/G | 2 | 5'-Ac CCT GCC CA-gel (SEQ ID NO:47) | +136 |

TABLE 4

The effect of the position of the allele base
within 10-mers on mutation detection.

| Position allele | 19-mer | | | RNA | | |
|---|---|---|---|---|---|---|
| | $T_{0.1}$ of perfect | $T_{0.1}$ of (G-A) | $\Delta T_{0.1}$ | $T_{0.1}$ of perfect | $T_{0.1}$ of (G-A) | $\Delta T_{0.1}$ |
| 9 | 40 | 32 | 8 | 35 | 37 | −2 |
| 8 | 47 | 32 | 15 | 49 | 38 | 11 |
| 7 | 42 | 30 | 12 | 44 | 41 | 3 |
| 6 | 47 | 28 | 19 | 49 | 41 | 8 |
| 5 | 52 | 38 | 14 | 50 | 42 | 8 |
| 4 | 54 | 39 | 15 | 54 | 44 | 10 |
| 3 | 55 | 46 | 9 | 59 | 54 | 5 |
| 2 | 52 | 46 | 6 | 58 | 53 | 5 |

TABLE 5

Identification of β-thalassemia
mutations by hybridization with the microchip.

| | | | Immobilized 10-mer oligonucleotide | | | | | | | | | | |
|---|---|---|---|---|---|---|---|---|---|---|---|---|---|
| Hybridized Probe | | | IVS (N) | I/1 G/A | I/1 G/T | I/2 T/A | I/2 T/C | I/2 T/G | I/2 G/A | I/5 G/G | I/5 G/T | I/6 T/C | CD26 (N) | CD26 G/A |
| | | Size | R at Td= | | | | | | | | | | | |
| # | Allele | (nt) | 42° C. | 39° C. | 38.5° C. | 42° C. | 48° C. | 45.5° C. | 37° C. | 44.5° C. | 40° C. | 50° C. | 54.5° C. | 49° C. |
| 1 | | | | | | | | | | | | | | |
| a | IVS (N) | 75 | 1.00 | 0.04 | 0 | 0.20 | 0.05 | 0.07 | 0 | 0 | 0 | 0.04 | 1.0 | — |
| b | IVS (N) | 19ª | 1.00 | 0.09 | 0.07 | 0.02 | 0.03 | 0.01 | 0.03 | 0.03 | 0.07 | ND | 0 | 0 |
| 2 | | | | | | | | | | | | | | |
| a | IVS I/2 T/A | F1 75 | 0.15 | 0 | 0 | 1.00 | 0.12 | 0.08 | 0 | 0 | 0 | 0 | 1.00 | — |
| b | IVS I/2 T/A | F1 133 | 0.03 | 0 | 0 | 1.00 | 0 | 0.30 | 0 | 0 | 0 | 0 | 1.00 | 0.19 |
| c | IVS I/2 T/A | 19ª | 0.01 | 0 | 0 | 1.00 | 0.07 | 0.03 | 0 | 0 | 0 | 0 | 0.01 | 0 |
| 3 | | | | | | | | | | | | | | |
| a | IVS I/2 G/A | 133f r | 0.03 | 1.00 | 0 | 0.01 | 0 | 0.02 | 0 | 0 | 0 | 0 | 1.0 | — |
| b | IVS I/2 G/A | 19ᶜ | 0.01 | 1.00 | 0.01 | 0.01 | 0 | 0 | 0.01 | 0 | 0 | 0 | 0 | 0 |
| 4 | | | | | | | | | | | | | | |
| a | IVS I/2 G/A & IVS I/6 T/C | 133f r | 0.2 | 0.85 | 0 | 0.2 | 0 | 0.05 | 0 | 0 | 0 | 1.00 | 1.00 | — |
| b | IVS I/2 G/A | 19ᶜ | 0.01 | 1.00 | 0.01 | 0.01 | 0 | 0 | 0.01 | 0 | 0 | 0 | 0 | 0 |
| c | IVS I/2 T/C | 19ª | 0.1 | 0 | 0 | 0 | 0 | 0 | 0 | 0 | 0 | 1.0 | 0 | 0 |
| a | IVS I/5 G/T | 19ª | 0 | 0 | 0 | 0 | 0 | 0 | 0.03 | 0.02 | 1.00 | 0 | 0 | 0 |
| 5 | | | | | | | | | | | | | | |
| b | CD26 (N) | 19ᶜ | 0 | 0 | 0 | 0 | 0 | 0 | 0 | 0 | 0 | 0 | 1.00 | 0.03 |
| c | CD26 G/A | 19ª | 0.0 | 0 | 0 | 0 | 0 | 0 | 0 | 0 | 0 | 0 | 0.04 | 1.00 |

TABLE 5-continued

Identification of β-thalassemia mutations by hybridization with the microchip.

| | | Immobilized 10-mer oligonucleotide | | | | | | | | | | |
|---|---|---|---|---|---|---|---|---|---|---|---|---|
| Hybridized Probe | | IVS (N) | I/1 G/A | I/1 G/T | I/2 T/A | I/2 T/C | I/2 T/G | I/5 G/A | I/5 G/G | I/5 G/T | I/6 T/C | CD26 (N) | CD26 G/A |
| | Size | R at Td= | | | | | | | | | | | |
| # Allele | (nt) | 42° C. | 39° C. | 38.5° C. | 42° C. | 48° C. | 45.5° C. | 37° C. | 44.5° C. | 40° C. | 50° C. | 54.5° C. | 49° C. |
| 6 | | | | | | | | | | | | | |
| a IVS (N) | 75 | 1.00 | 0.04 | 0 | 0.20 | 0.05 | 0.07 | 0 | 0 | 0 | 0.04 | 1.00 | — |
| b IVS I/2 T/A | F1 133 | 0.03 | 0 | 0 | 1.00 | 0 | 0.30 | 0 | 0 | 0 | 0 | 1.00 | — |

The noticeable exceptions are oligonucleotides corresponding to IVS ½ T/A and IVS ½ T/G mutations that show strong mismatched signals upon hybridization with non-corresponding samples of IVS (N) and IVS ½ T/A RNA's, respectively (Table 5, 1a, 2b, 4a, 6a and 6b). The relative intensities of these mismatched signals can be significantly decreased by choosing the proper oligonucleotides for immobilization. It appears that the diagnostic assays can be carried out with RNAs 75 nucleotides (nt) long (Table 5, probes 1a, and 6a), and 133 nt long (probes 2a and 6b), as well as with 133 nt long RNA fragmented to pieces 20–40 nt long (probes 3a and 4a). However, the intensities of the hybridization signals after fragmentation are increased by about 5 times and the time of hybridization is decreased from several hours to a tens of minutes.

The longer RNA probes diffuse more slowly into the gel and can form stable secondary structures or aggregates. These factors interfere with their hybridization with rather short immobilized oligonucleotides. Thus, the fragmentation seems to be an essential step in sample preparation, since it enhances and speeds the hybridization.

In addition to the measuring of the melting curves, the reliability of identification of mutations and base changes can be enhanced by the use of a multicolor fluorescence microscope (Yershov et al., 1996). For this purpose, the tested RNA is marked by one fluorescence label and is hybridized with a microchip in the presence of a normal allele sample labeled with a different dye. The pattern and the ratio of hybridization measured with the two dyes will be similar for all microchip oligonucleotides except for those that correspond to different allele bases, i.e., mutations. Table 4 shows the results of such an experiment. The patterns of hybridization detected at two wavelengths are very similar.

As shown in Table 3, the immobilized 10-mers matching the mutations IVS I-2 T/G, IVS I-2 T/C, and IVS I-2 T/A are hybridized rather strongly with some RNA probes that correspond to other alleles. Different structural factors in RNA could cause this hybridization. The effect of these factors can be minimized by placing a variable IVS I-2 base into different positions of the 10-mers. The results of such experiments are shown in Table 4. Microchip II was successively hybridized with fragmented 75-nt-long RNA or with a synthetic DNA 19-mer, both corresponding to the normal allele. Microchip II contained two similar sets of eight overlapped immobilized 10-mers that are complementary either to a normal allele or to IVS I-2 T/G allele. The allele specific bases A for the first set and C for the second set are located in these 10-mers in all internal positions from the $2^{nd}$ to the $9^{th}$. These bases form perfect A-T or mismatched A-G base pairs, respectively. The stability of the perfect and mismatched duplexes formed on the microchip is determined as $T_{0.1}$ the temperature at which the initial hybridization signal of the duplex is decreased to one-tenth of the original intensity. $\Delta T_{0.1}$ corresponds to the difference in $T_{0.1}$ between the perfect and similar mismatched duplexes. A better discrimination of the perfect and mismatched duplexes is reflected in higher values of $\Delta T_{0.1}$. The discrimination efficiency ($\Delta T$) was lower for hybridized RNAs than for the 19-mers. The discrimination was surprisingly low, $\Delta T = -2°$ and $3°$ C., when the allelic bases were placed at the $9^{th}$ or $7^{th}$ position, respectively, of the immobilized oligonucleotides. It appears that secondary structures and the presence of similar sequences in other regions of the RNA causes this lowering. These effects can be partly predicted from the sequence of the region that is searched for mutations. However, it is impossible to reach a high discrimination ($\Delta T = 8-11°$ C.) when allele bases are placed in other positions, for example the 8, 6, 5, or 4 positions.

The hybridization of RNA transcripts of PCR-amplified DNA with oligonucleotide microchips allows the reliable identification of base changes and discrimination of homozygous and heterozygous β-thalassemia mutations in the genomic DNA of patients.

RNA transcribed from PCR-amplified DNA provides an easier method for preparing a sufficient amount of labeled, single-stranded samples than the use of DNA prepared by PCR amplification. RNA can be fragmented and one fluorescent dye molecule can be introduced per fragment.

Example 7

Use of a Customized Microchip Biosensor to Detect Gene Expression

Gene expression is one of the central themes in modern molecular biology. DNA from well studied genetical sources has already been systematically sequenced. For these sequences hybridization procedures are successfully used to estimate a level of differential gene expression. The results of this estimation are useful for understanding fundamental mechanisms of development biology, embryology and treatment of genetic and infectious diseases.

To determine whether oligonucleotide microchips are useful to identify gene expression, microchip biosensor hybridization was carried out with ssDNA fragments isolated from six different genes:

205 b fragment from glyceraldehyde 3-phosphate dehydrogenase (G3PDH);
281 b fragment from human transferrin receptor (HTR);
224 b fragment from human $\beta_2$-microglobulin (B2M);
545 b fragment from human interleukin-1 receptor (IL1R);
188 b fragment from human NF-kB (p50);
224 b fragment from human interferon y receptor (IGR).

Figure 8:
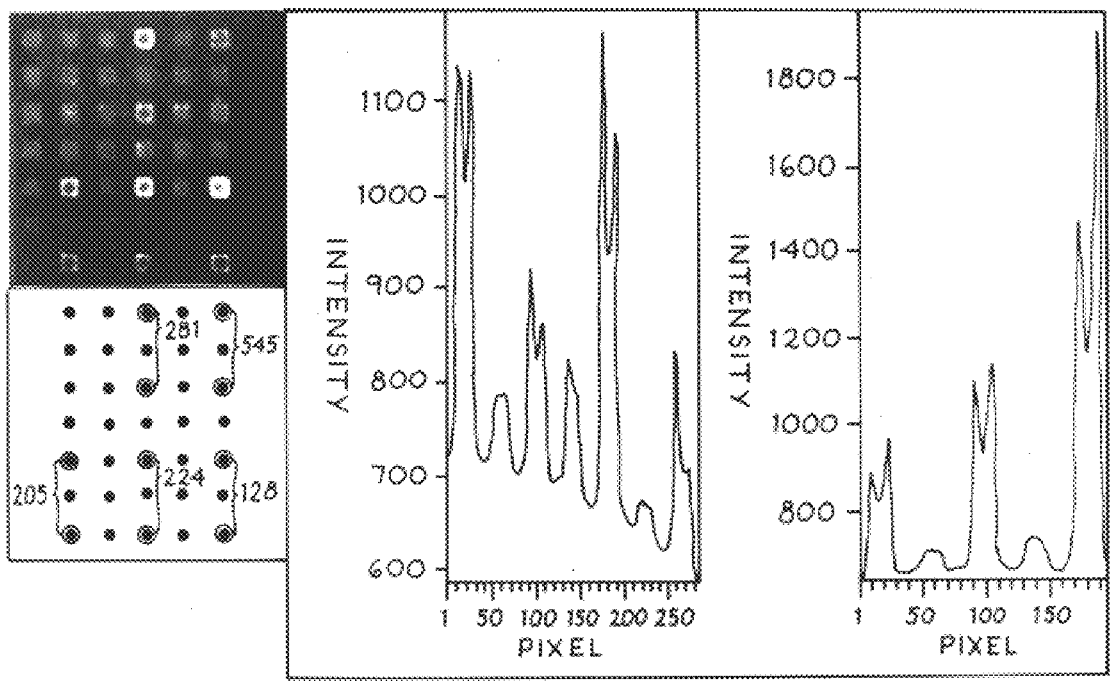
FIG. 8 shows results of gene expression studies.

A customized microchip, containing immobilized 60 b oligonucleotides, having at the 3'-terminal position 3-methyluridine residues, corresponding to five housekeeping genes (G3PDH, HTR, B2M, IL1R and NF-kb(p50)) (CLONTECH catalog 94/95 "Tools for the Molecular Biologist", pp. 90–93) were produced for hybridization experiments with complementary ssDNA fragments. Each oligonucleotide was applied at two positions on the microchip in a 1:10 ratio of amount (0.3 pmol:0.03 pmol each). ssDNA fragments complementary to immobilized oligonucleotides were synthesized by asymmetric PCR amplification (using only one primer) with fluorescently labeled nucleotide triphosphates (FUORscript T7, Fluorescein-Labeling In Vitro Transcription Kit). Moreover, the PCR-primer bore a biotin tag that was utilized for following isolation of synthesized ssDNA fragments with avidin carried on a column (Sambrook et al. "Molecular Cloning" 2d edit., p. 12.14). FIG. 8 demonstrates hybridization on the microchip. Intensity of fluorescence in each spot depends on the amount of immobilized oligonucleotide and on the length of the DNA fragment in the spot. For hybridization, 10 $\mu$l of Buffer A (50% formamide, 10% dextran sulfate, 1% SDS, 50 mM sodium phosphate at pH 7.4, 750 mM sodium chloride, 5 mM sodium EDTA) containing ssDNA with a concentration of 0.5 pmol/$\mu$l (approximately 0.05 $\mu$g/$\mu$l) was incubated for about 6–12 h at room temperature, washed briefly with $H_2O$ and analyzed with a fluorescent microscope. Before rehybridization the microchip was treated in Buffer B (50% formamide, 1% Tween 20) for 30 min. at 50° C. to completely remove hybridized ssDNA.

These results indicate that concentration of fluorescently labeled ssDNA may be decreased up to 100 fold. Hybridization with individual ssDNA fragments indicates high specificity of studied oligonucleotides. There was no cross-hybridization detected between different tested DNAs and immobilized oligonucleotides. None of the oligonucleotides demonstrated a signal when hybridized with non-specific DNA (e.g. probe IGR). This differentiates "expression" of non-expressed genes from expression of housekeeping genes. Genes that are not expressed in a particular cell or tissue, may actually be picked up in conventional screening procedures as having a low expression, while other genes being expressed in all cells (housekeeping genes) will also be picked up as having low to moderate expression. The housekeeping genes are actually being expressed. In this example a difference in signal is detectable so that low level expression could be unambiguously distinguished from low level background.

The procedure detects expression of genes of high and middle expression level. To determine low level gene expression selective RT-PCR amplification is preferred.

Example 8

Use of a Customized Microchip Biosensor of the Present Invention to Detect HLA Polymorphisms A difficult problem of genotype recognition arises in studying different haplotypes (alleles) of genes encoding Human Leucocyte Antigens (HLA) in regions of histocompatibility genes. The HLA locus (class I and class II genes) is responsible for histocompatability of tissue transplantation. The need for allele identification is encountered also in various medical and biological tasks involving HLA class II genes. There are many clinical data showing strong association between HLA genotype and susceptibility to some disorders, for example some alleles DQA1/DQB1 are clearly related to IDDM (Insulin—Dependent Diabetes Mellitus), malaria, autoimmune diseases, such as rheumatoid arthritis and pemphigus vulgaris—a skin disease which causes severe blistering. The high level of polymorphism of HLA has been shown to be useful for identification of individuals determining the group of risk for some diseases. HLA typing is particularly crucial for matching donors for transplants. It is also proposed for infertility work-ups.

In this aspect, the present invention provides a method which allows an array of immobilized 8–12 long oligonucleotides to form an oligonucleotide microchip thereby facilitating identification of HLA DQA1 allies.

An algorithm has been designed and special computer programs have been constructed which allow the analysis of the nucleotide sequences of all alleles of various HLA subloci. Forming an optimized set of oligonucleotides provides high reliability of detection of homo- and heterozygotes for the HLA alleles.

A customized microchip, containing an array of eighteen PAA—gel immobilized (1 pmol of each) short oligonucleotides has been produced for hybridization with fluorescently labelled complementary HLA DQA1 DNA or RNA probe for allele identification. 18 decamers were loaded on the chip in the following order, from left to right:

TABLE 6

| first (upper) row | 1 | 2 | 3 | 4 | $G^4$-control oligo |
|---|---|---|---|---|---|
| Second: | 5 | 6 | 7 | 8 | $G^3$-control oligo |
| Third: | 9 | 10 | 11 | 12 | 13 |
| 4-th: | 14 | 15 | 16 | 17 | 18 |

The sequence of the oligos used was as shown in FIG. 9.

The oligonucleotides immobilized on the microchip are complementary to the sense strand of different alleles of DQA1 DNA and some control oligos. A microchip with 20 oligonucleotides was manufactured for partial identification of 15 different alleles in the HLA DQA1 region. PCR was used to prepare 229 bp (starting from condon 12 to condon 87) DNA fragments of the polymorphic second exon of the DQA1 gene from human genomic DNA. Nested primers were used 2DQAAMP-A:5'-a t ggt gta aac ttg tac cag t (SEQ ID NO:73); and 2DQAAMP-B:5'tt ggyt agc agc ggt aga gtt g (SEQ ID NO:74). Nested PCR primers were: T7-2DQAAMP-A and primer B. The first primer containing the promoter for T7 RNA polymerase and PCR product were used for in vitro transcription. RNA probes were identical to the coding DNA strand. RNA was fragmented, labeled with fluorescein and used for hybridization with the microchip. Hybridization conditions were as follows: overnight incubation at 5° C. in 1M NaCl, 1 mM EDTA, 5 mM Na-phosphate, pH 7.0, 1% Tween 20. The temperature was then increased stepwise at 10° C. intervals, and fluorescence measurements were taken at each step. BUFFER WAS NOT CHANGED.

Figure 10:
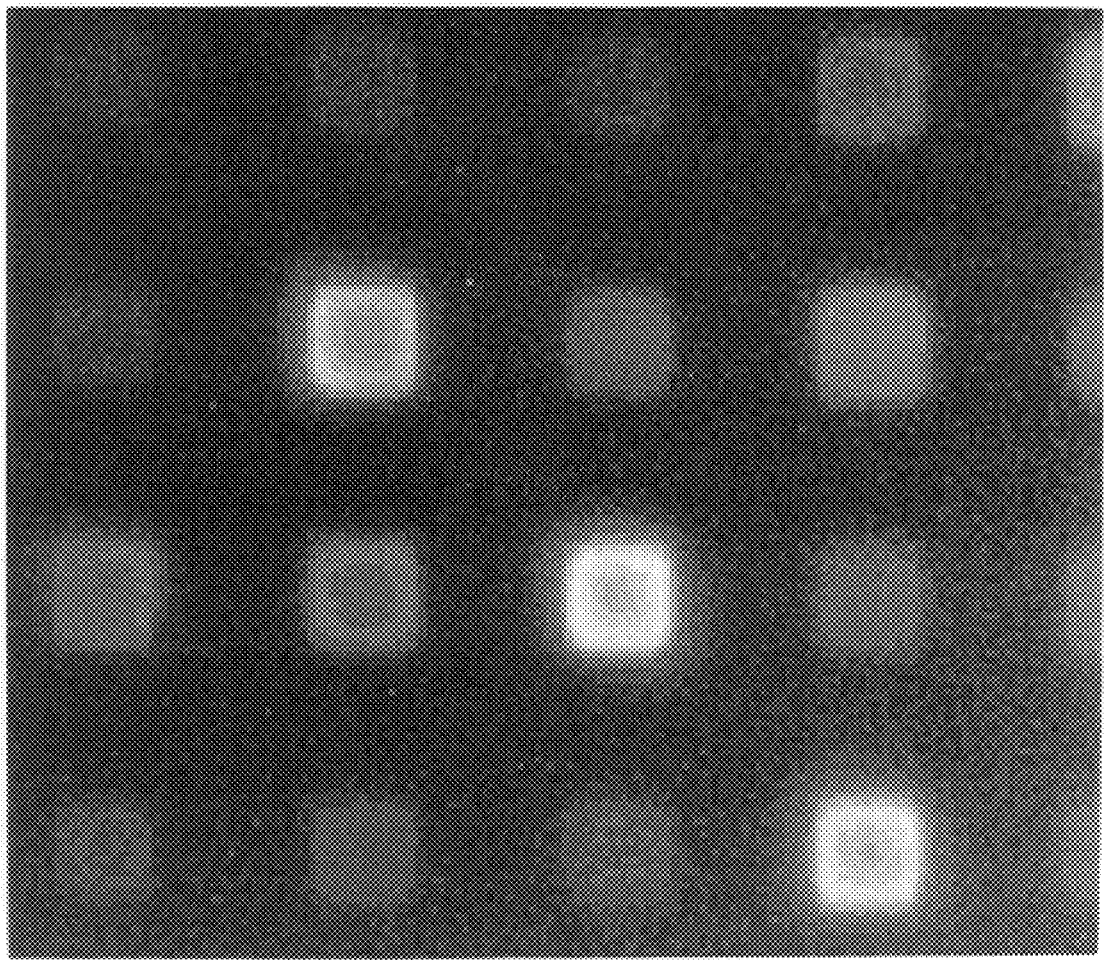
FIG. 10 shows HLA oligonucleotides hybridized to the microchips.
Figure 11:
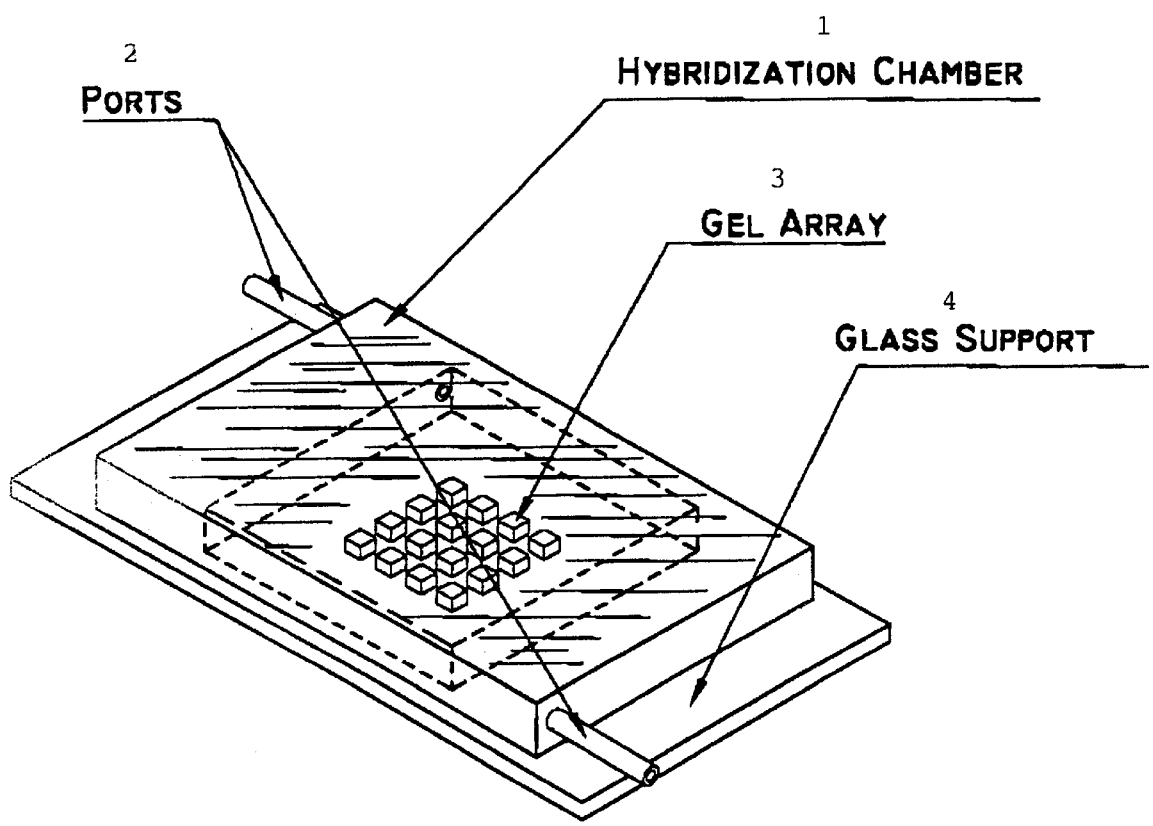
FIG. 11 illustrates a closed microchamber 1 containing a microchip with a gel array 3 on a glass support 4; ports 2 are used merely to provide wetting solution.
Figure 12:
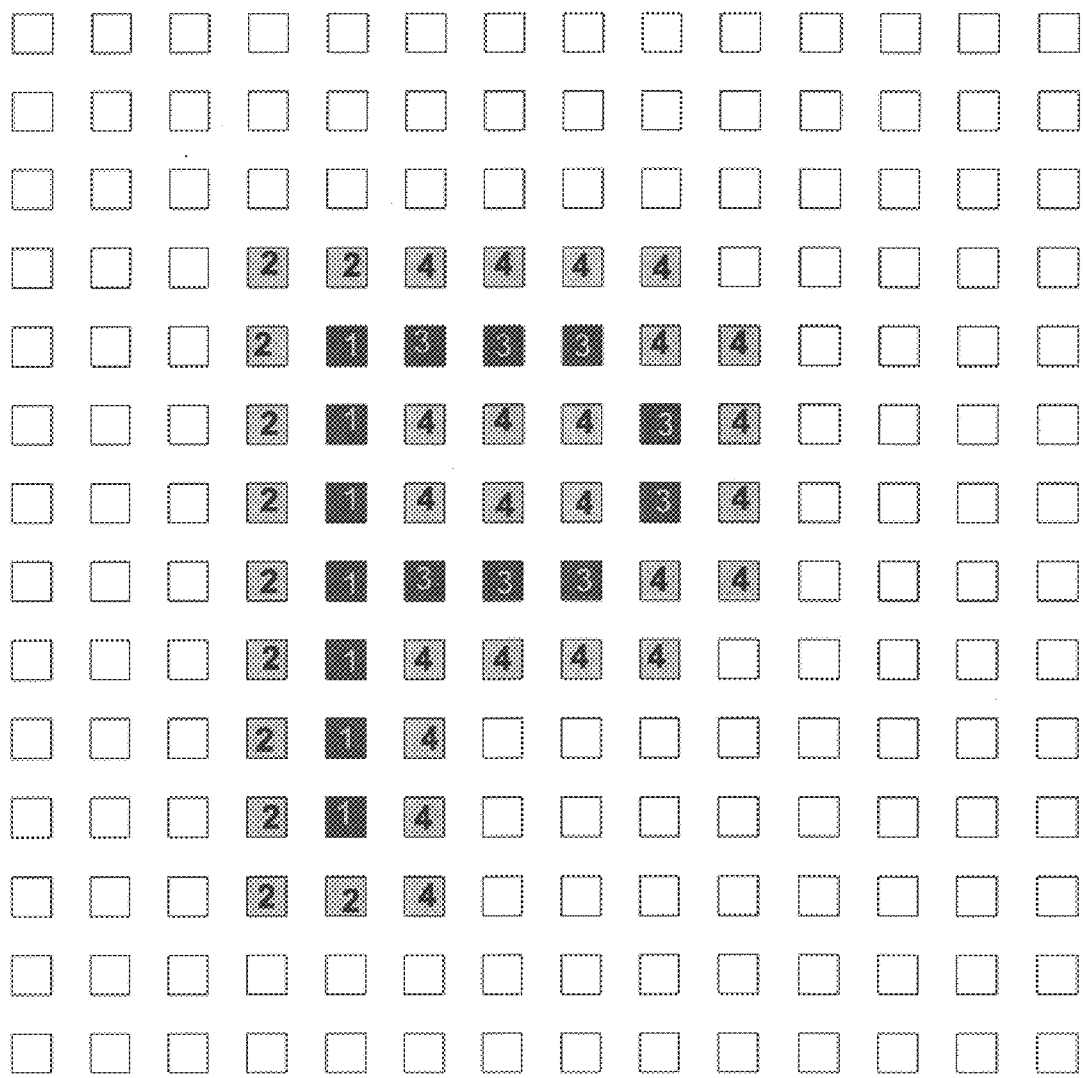
FIG. 12 shows an ordered scheme in which a letter "P" will be detected if there is a group of hybridizations of oligonucleotides from a sample that are oligonucleotides from pathogens.

FIG. 10 shows the hybridization results and presents schematically the HLA DQA1—chip for allele identification. In FIG. 10 three diagonally placed oligos (11-0101/0104 allele specific; 6-specific for 0101,01021,01022,0103, 00104; 17-correspond to all alleles, except 0502) gave a positive hybridization signal, and are observed as three diagonally placed bright fluorescence spots. The probes were identified as the 0101 or 0104 allele (both alleles are identical in the second exon). All other oligos yielded much weaker fluorescence signals compared with those described above, because none of them contain sequences complementary to alleles 0101 and 0104. On the other hand any allele different from 0101 or 0104, reveals another set of hybridization signals.

The brightest fluorescent squares on the chip were: Oligo#4 which is 03011 or 0302 specific; oligo#8 is Taq polymerase-specific artifacts; oligo#18-belong to alleles 0101-05011; oligo 11-0101,0104 allele specific; 17—corresponds to all alleles, except 0502; g4 is a fluorescent control oligo; #13—mismatch to #18. All other chip elements showed significantly less intensive fluorescence. The genotype identified by these probes has a 0101/0104-0302/03011 heterozygote.

Example 9

Use of a Customized Microchip Biosensor to Detect the Lyme Disease Spirochetes

Bacteria belonging to the species *Barretia burgdorferi* and related species of tick-borne spirochetes are capable of causing human and veterinary disease. Nucleic acid probes are available to detect bacteria causing Lyme disease. These bacteria cannot be identified by standard microbiological methods, although immunological tests are available.

Using the methods of the present invention, oligonucleotides are prepared according to Weisburg (1995) and added to a micromatrix designed for use in detecting Lyme disease in a clinical sample.

Example 10

Use of a Customized Microchip Biosensor to Detect Salmonella In Food Samples

Salmonella presence is detected most commonly by preparing cultures according to standard microbiological laboratory procedures, and testing the cultures for morphological and biochemical characteristics. After about 48 hours after collection of a sample testing begins and takes several days to complete.

However, RNA and DNA probes for Salmonella testing are available. Using the methods of the present invention, oligonucleotides are prepared according to Lane et al. (1996) incorporated herein by reference and added to a microchip designed for use in detecting Salmonella in food samples by distinguishing rRNA of Salmonella from non-Salmonella.

DOCUMENTS CITED

AUSUBEL, F. M., R. BRENT, R. E. KINGSTON, D. D. MORE, J. G. SEIDMAN, J. A. SMITH, and K. STRUHL, Eds., ed. (1994) Current Protocols in Molecular Biology. Greene Wiley Interscience: New York, N.Y.

BEATTIE, K. L., BEATTIE, W. G., MENG, L., TURNER, S. L., CORAL-VAZQUEZ, R., SMITH, D. D., McINTYRE, P. M. and DAO, D. D.: Advances in Genosensor Research. Clin. Chem. 41/5 (1995) 700–706.

CONNER, B. J., REYERS, A. A., MORIN, C., ITAKURA, K., TEPLITZ, R. L. and WALLACE, R. B. (1983) Detection of sickle cell β-globin allele by hybridization with synthetic oligonucleotides. Proc. Natl. Acad. Sci. USA 80: 278–282.

DIAZ-CHICO, J. C., YANG, K.-G., YANG, K.-Y., EFREMOV, D. G., STOMING, T. A. and HUISMAN, T. H. (1988) J. Biochim. Biophys. Acta 949: 43–48.

FODOR, S. P. A., READ, J. L., PIRRUNG, M. C., STRYER, L., LU, A. T. and SOLAS, D.: Light-directed, spatially addressable parallel chemical synthesis. Science 251 (1991) 767–773.

GHU, Z., GUILFOYLE, R. A., THIEL, A. J., WANG, R., and SMITH, L. M.: Direct fluorescence analysis of genetic polymorphisms by hybridization with oligonucleotide arrays on glass support. Nucl. Acids Res. 22 (1994) 5456–5465.

KHRAPKO, K., LYSOV, YU. KHORLIN, A., IVANOV, I., YERSHOV, G., VASILENKO, S., FLORENTIEV, V., and MIRZABEKOV, A. (1991) A method for DNA sequencing by hybridization with oligonucleotide matrix. J. DNA Sequencing 1 375–388.

KHRAPKO, K. R. et al. (1996) U.S. Pat. No. 5,552,270.

LAMTURE, J. B., BEATTIE, K. L., BURKE, B. E., EGGERS, M. D., EHRLICH, D. J., FOWLE, R., HOLLIS, M. A., KOSICKI, B. B., REICH, R. K., SMITH, S. R., VARMA, R. S. and HOGAN, M. E.: Direct detection of nucleic acid hybridization on the surface of a charge-coupled device. Nucl. Acids Res. 22 (1994) 2121–2125.

LANE, D. J. et al. (1996) Oligonucleotide Probes for Detection of Salmonella, U.S. Pat. No. 5,495,008.

LAWN, R. EFSTRATIADIS, A., O'CONNEL, C., and MANIATIS, T. (1980) The nucleotide sequence of the human β-globin gene. Cell 21: 647–651.

LESNIK, E. A., and FREIER, S. (1995) Relative thermodynamic stability of DNA, RNA, and DNA:RNA hybrid duplexes: relationship with base composition and structure. Biochemistry 34: 10807–10815.

LIPSHUTZ, R. J., MORRIS, D., CHEM, M., HUBBELL, E., KOZAL, M. J., SHAH, N., SHEN, N., YANG, R. and FODOR, S. P. A. (1995) Using oligonucleotide probe arrays to access genetic diversity. BioTechniques 19: 442–447.

MAIDAK, B. C. et al. (1996) The ribosomal database project (RDP), Nucleo Acids Res. 24:82–85.

MATSON, R. S., RAMPAL, J., PENTONEY, S. L., ANDERSON, P. D. and COASSIN, P.: Biopolymer synthesis on polypropylene support: oligonucleotide arrays. Anal. Biochem. 224 (1995) 110–116.

MIRZABEKOV, A. (1994) DNA Sequencing by hybridization: a megasequencing method and a diagnostic tool? Trends in Biotechnology 12: 27–32.

MOBARRY, B. K. et al. (1996) Phylogenetic probes for analyzing abundance and spatial organization of nitrifying bacteria. *Appl. Environ. Microbiol.* 62:2156–2162.

PEASE, A. C., SOLAR, D., SULLIVAN, E. J., CRONIN, M. T., HOLMES C. P. and FODOR, S. P. A.: Light-directed oligonucleotide arrays for rapid DNA sequence analysis. Proc. Natl. Acad. Sci. USA 91 (1994) 5022–5026.

PONCZ, M. SOLOWIEJCZYK, D. and HARPEL, B.(1982) Construction of human gene libraries from small amount of peripheral bloods: analysis of β-like globin genes. Hemoglobin 6: 27–40.

STAHL, D. A. (1995) Application of phylogenetically based hybridization probes to microbial ecology. *Mol. Ecol.* 4:535–542.

SOUTHERN, E. M. (1996) DNA chips: analyzing sequence by hybridization to oligonucleotides on a large scale, TIG 12:110–115.

SOUTHERN, E. M., MASKOS, U. and ELDER, J. K.: Analyzing and comparing nucleic acid sequences by hybridization to arrays of oligonucleotides: evaluation using experimental models. Genomics 13 (1992) 1008–1017.

WAGNER, M. et al. (1995) In situ identification of amoniaoxidizing bacteria. Sept. Appl. Microbiol 18: 251–264.

WEISBURG, W. G. (1995) Nucleic Acid Probes for the Detection of Lyme Disease Spirochetes, U.S. Pat. No. 5,466,577.

WOESE, C. R. (1987) Bacterial evolution, Microbial. Rev. 51:221–271.

YERSHOV, G., BARSKY, V., BELGOVSKIY, A., KIRILLOV, E., KREINDLIN, E., IVANOV, I., PARINOV, S., GUSHIN, D., DROBYSHEV, A., DUBILEY, S., and MIRZABEKOV, A. (1996) DNA analysis and diagnostics on oligonucleotide microchips. Proc. Natl. Acad. Sci. USA 93: 4913–4918.

U.S. Pat. No. 5,552,270.

We claim:

1. A method for using a reuseable microchip to identify at least one nucleic acid sequence in nucleic acids of a sample, said method comprising:

(a) providing a customized matrix of oligonucleotides on the microchip in an arrangement that is an ordered scheme designed to present a detectable pattern as a whole that identifies the sequences of nucleic acids in the sample;

(b) hybridizing nucleic acids from the sample on said microchip; and (c) identifying at least one nucleic acid sequence in said sample by the pattern detected as a whole on the microchip, said pattern resulting from the locations of oligonucleotides which hybridized to the sample nucleic acids wherein the customized matrix of oligonucleotides on the reusable microchip is formed by a plurality of gel elements, wherein the number of elements is determined by the number of oligonucleotides in the matrix and wherein each gel element contains one oligonucleotide of a desired nucleic acid sequence length and concentration, each gel element being separated from another by interstitial spaces, said oligonucleotides being positioned in specific locations and wherein said matrix comprises oligonucleotides comprising the base sequences:

| Oligonucleotide Name and Position | Sequence (5' to 3') | |
|---|---|---|
| Nb1000 | TGC GAC CGG TCA TGG | (SEQ ID: 6) |
| NIT3 | CCT GTG CTC CAT GCT CCG | (SEQ ID: 7) |
| NEU23 | CCC CTC TGC TGC ACT CTA | (SEQ ID: 8) |
| NSO190 | CGA TCC CCT GCT TTT CTC | (SEQ ID: 9) |
| NSO1225 | CGC GAT TGT ATT ACG TGT GA | (SEQ ID NO: 10) |
| NSMO156 | TAT TAG CAC ATC TTT CGA T | (SEQ ID NO: 11) |
| NSV443 | CCG TGA CCG TTT CGT TCC | (SEQ ID NO: 12) |
| BAC338 | GCT GCC TCC CGT AGG GAT | (SEQ ID NO: 13) |
| NonBAC338 | ACT CCT ACG GGA GGC AGC | (SEQ ID NO: 14) |
| UNI1390 | GAC GGG CGG TGT GTA CAA | (SEQ ID NO: 15) |

2. The method of claim 1, wherein the oligonucleotides are arranged in a matrix wherein I, II, III and IV are columns and "ABC" are rows in a microchip:

| | I | II | III | IV |
|---|---|---|---|---|
| A | Nb1000 | NIT3 | NEU23 | Nso190 |
| B | Nso1225 | Nsm156 | Nsv443 | |
| C | Bac338 | NonBac338 | Uni1390 | |

3. The method of claim 1, further comprising:

adding a label to the nucleic acid sequences in said sample before hybridizing them to oligonucleotides in the microchip.

4. The method of claim 3, wherein the label is a fluorescent dye.

5. The method of claim 3, wherein the label is a plurality of different dyes.

6. A microchip matrix for the detection and classification of nitrifying bacteria wherein said matrix has the following design:

| | I | II | III | IV |
|---|---|---|---|---|
| A | Nb1000 | NIT3 | NEU23 | Nso190 |
| B | Nso1225 | Nsm156 | Nsv443 | |
| C | Bac338 | NonBac338 | Uni1390 | | wherein I, II, III and IV are columns and A, B, C, are row in a microchip, and wherein the base sequences are:

| Oligonucleotide Name and Position | Sequence (5' to 3') | |
|---|---|---|
| Nb1000 | 5'-TGC GAC CGG TCA TGG-3' | (SEQ ID NO: 6) |
| NIT3 | 5'-CCT GTG CTC CAT GCT CCG-3' | (SEQ ID NO: 7) |
| NEU23 | 5'-CCC CTC TGC TGC ACT CTA-3' | (SEQ ID NO: 8) |
| NS0190 | 5'-CGA TCC CCT GCT TTT CTC- 3' | (SEQ ID NO: 9) |
| NS01225 | 5'-CGC GAT TGT ATT ACG TGT GA-3' | (SEQ ID NO: 10) |
| NSM0156 | 5'-TAT TAG CAC ATC TTT CGA t-3' | (SEQ ID NO: 11) |
| NSV443 | 5'-CCG TGA CCG TTT CGT TCC- 3' | (SEQ ID NO: 12) |
| BAC338 | 5'-GCT GCC TCC CGT AGG GAT-3' | (SEQ ID NO: 13) |
| NonBAC338 | 5'-ACT CCT ACG GGA GGC AGC-3' | (SEQ ID NO: 14) |
| UNI1390 | 5'-GAC GGG CGG TGT GTA CAA-3' | (SEQ ID NO: 15) |

* * * * *

UNITED STATES PATENT AND TRADEMARK OFFICE
CERTIFICATE OF CORRECTION

PATENT NO. : 6,458,584 B1
DATED : October 1, 2002
INVENTOR(S) : Mirzabekov et al.

It is certified that error appears in the above-identified patent and that said Letters Patent is hereby corrected as shown below:

Title page,
Item [56], OTHER PUBLICATIONS,
"Amann, R.I. et al. (1990)," reference, after "Analyzing", please insert -- Mixed --
"Beattie, K.L. et al. (1995)," reference, please change "705" to -- 706 --
"Mobarry, B.K. et al. (1996)," reference, please change "1262" to -- 2162 --

Drawings,
Sheet 14, row 1, after "positive for B. Anthracis", please insert -- (SEQ ID NO: 75) --
Sheet 14, row 2, after "negative for B. Anthracis", please insert -- (SEQ ID NO: 76) --
Sheet 14, row 3, after "positive for B. Anthracis", please insert -- (SEQ ID NO: 77) --
Sheet 14, row 4, after "negative for B. Anthracis", please insert -- (SEQ ID NO: 78) --

Column 1,
Line 17, after "pattern", please insert -- . --

Column 3,
Line 2, please change "multiples" to -- multiple ---

Column 6,
Line 19, please change "thousand" to -- thousands --

Column 8,
Line 54, please change "RNA" to -- rRNA --

Column 9,
Line 25, after "tumors", please insert -- , --

Column 13,
Line 55, please change "52°" to -- 52°C --
Line 55, please change "64°" to -- 64°C --

UNITED STATES PATENT AND TRADEMARK OFFICE
CERTIFICATE OF CORRECTION

PATENT NO. : 6,458,584 B1
DATED : October 1, 2002
INVENTOR(S) : Mirzabekov et al.

It is certified that error appears in the above-identified patent and that said Letters Patent is hereby corrected as shown below:

Column 14,
Line 2, please change "10°" to -- 10°C --
Line 13, please change "extend" to -- extent --

Column 15,
Line 21, please change "rRNA's" to -- rRNAs --

Columns 15 & 16,
TABLE 2, column Oligonucleotide Name and Position, please change "NS0190" to -- NSO190 --
TABLE 2, Oligonucleotide Name NSMO156, column Sequence (5' to 3'), after "3'", please delete "?"

Column 18,
Line 34, after "4A", please insert -- ) --
Line 39, please change "nitrosovibrio" to -- Nitrosovibrio --
Line 42, please change "nitrosovibrio" to -- Nitrosovibrio --
Line 53, please change "difference" to -- differences --
Line 58, please change "oligonucleotides" to -- oligonucleotide --

Column 19,
Line 44, please change "DATP" to -- dATP --
Line 56, please change "fives" to -- five --

Column 20,
Line 42, please change "thermotable" to -- thermostable --

Column 21,
Line 31, please change "10O1H10OH20" to -- 100H100H20 --

Column 22,
Line 33, after "mg", please insert -- of --
Line 34, before "DNA", please delete "of"
Line 42, please change "MM" to -- mM --
Line 42, please change "M9C1$_2$" to -- MgCl$_2$ --

UNITED STATES PATENT AND TRADEMARK OFFICE
CERTIFICATE OF CORRECTION

PATENT NO.    : 6,458,584 B1
DATED         : October 1, 2002
INVENTOR(S)   : Mirzabekov et al.

It is certified that error appears in the above-identified patent and that said Letters Patent is hereby corrected as shown below:

Column 24,
TABLE 3, MICROCHIP I, row 6, column Sequence, please change
"G'-ATACCacCCT-gel" to -- 5'-ATACCACCCT-gel --

Column 27,
Line 24, please change "RNA's" to -- RNAs --

Columns 27 and 28,
TABLE 5, column Allele, row # 3a, please change "IVS I/2" to -- IVS I/1 --
TABLE 5, column Allele, row # 3b, please change "IVS I/2" to --IVS I/1 --
TABLE 5, column Allele, row # 4a, please change "IVS I/2" to --IVS I/1--
TABLE 5, column Allele, row # 4b, please change "IVS I/2" to --IVS I/1 --
TABLE 5, column Allele, row # 3a, please change "IVS I/2" to --IVS 1/6 --

Column 30,
Line 18, after "12", please insert -- bp --
Line 49, please change "condon" to -- codon --

Column 33,
Line 6, please change "amoniaoxidizing" to -- ammoniaoxidizing --

Column 60,
Claim 6, please change "row" to -- rows --
Claim 6, "Oligonucleotide NSM0156, column Sequence (5' to 3')", please change "t" to -- T --

Signed and Sealed this

Seventeenth Day of June, 2003

JAMES E. ROGAN
*Director of the United States Patent and Trademark Office*